(12) United States Patent
Duran Neira et al.

(10) Patent No.: US 8,312,768 B2
(45) Date of Patent: Nov. 20, 2012

(54) AUTONOMOUS AND REMOTE-CONTROLLED MULTI-PARAMETRIC BUOY FOR MULTI-DEPTH WATER SAMPLING, MONITORING, DATA COLLECTION, TRANSMISSION, AND ANALYSIS

(75) Inventors: Carlos Duran Neira, Santiago (ES); Xulio Fernandez Hermida, Vigo (ES)

(73) Assignee: Centro de Investigaciones Submarinas S.L., Santiago de Compostela (ES)

( * ) Notice: Subject to any disclaimer, the term of this patent is extended or adjusted under 35 U.S.C. 154(b) by 17 days.

(21) Appl. No.: 12/831,304

(22) Filed: Jul. 7, 2010

(65) Prior Publication Data

US 2011/0009019 A1    Jan. 13, 2011

Related U.S. Application Data

(60) Provisional application No. 61/224,557, filed on Jul. 10, 2009.

(51) Int. Cl.
*G01C 5/00* (2006.01)
(52) U.S. Cl. .................................... 73/170.29
(58) Field of Classification Search ................ None
See application file for complete search history.

(56) References Cited

U.S. PATENT DOCUMENTS

| | | | | |
|---|---|---|---|---|
| 4,754,654 A | * | 7/1988 | Johnson et al. | 73/864.34 |
| 5,816,874 A | | 10/1998 | Juran et al. | |
| 6,536,272 B1 | * | 3/2003 | Houston et al. | 73/170.29 |
| 2003/0092393 A1 | | 5/2003 | Tokhtuev et al. | |

* cited by examiner

*Primary Examiner* — Andre Allen
(74) *Attorney, Agent, or Firm* — Mateo Aboy; Aboy & Associates PC

(57) ABSTRACT

Disclosed embodiments include an apparatus for water sampling and analysis, the apparatus comprising: (a) a device for water sampling at a plurality of depths comprising a hosepipe and a plurality of internal independent pipes with a plurality of sampling inlets at a plurality of water depths, and (b) a pumping system to pump a sample of water collected using the device for water sampling at a plurality of depths to an isolated module for analysis. According to one embodiment, the apparatus is an autonomous multi-parametric buoy with capabilities for multi-depth water sampling, self-maintenance, monitoring, data collection, transmission, and analysis.

17 Claims, 23 Drawing Sheets

AUTONOMOUS AND REMOTE-CONTROLLED MULTI-PARAMETRIC BUOY FOR MULTI-DEPTH WATER SAMPLING, MONITORING, DATA COLLECTION, TRANSMISSION, AND ANALYSIS

CROSS-REFERENCE TO RELATED APPLICATIONS

This application claims the benefit of U.S. Provisional Application No. 61/224,557 filed on 2009 Jul. 10 by the present inventors, which is incorporated herein by reference.

TECHNICAL FIELD

This invention relates to water sampling devices. Specifically, it relates to devices such as buoys with water analysis and monitoring capabilities.

BACKGROUND

Traditional observation and measurement of physical, chemical, and biological properties of water in coastal and open ocean environments, lakes, rivers, and reservoirs has been carried out primarily by two techniques: 1) sensor devices directly immersed in the water, and 2) research vessels equipped with a plurality of sensing, analysis, and storage capabilities including computers for analysis, processing, and storage of analysis results.

Devices that include predefined sensors to periodically sample water such as drifters and monitoring buoys typically have a reduced lifetime due primarily to two reasons: 1) these systems are sensor-specific and new sensors cannot be easily incorporated without major system modifications involving significant, time consuming, and expensive engineering redesign, and 2) the sensors are immersed and directly exposed in the water which severely affects their useful working life due to the accumulation of organic and inorganic solid materials resulting in sensor malfunctions and unreliable readings within weeks. Consequently, the only way to guarantee reliable readings is to perform periodic maintenance of the buoys on a weekly basis. This requires a time consuming process involving accessing the buoy, collecting all the sensors immersed in water, cleaning the sensors, calibrating the sensors, and re-positioning each sensor at the correct immersion depth. This is a significant limitation since these monitoring buoys may be analyzing waters in locations of difficult access and often it is not possible to perform the scheduled maintenance due to difficult meteorological conditions. Maintenance is even more problematic in systems comprising a several of sensors connected to a line in order to sample water at several different of depths since each submerged sensor must be collected, cleaned, calibrated, and repositioned at the exact depth location.

In addition to the limitations related to the fact that current buoy-based monitoring systems immerse the sensors directly in the water to perform the sampling and the associated maintenance this design requires, other limitations include the maximum depth at which these sensors can be submerged and sample water.

Currently available systems and those disclosed in the art are limited to sampling and sensing close-to-surface-level waters. This limits the type of analytics they can handle and the domain of problems they can be used for.

Consequently, it is desirable to develop water monitoring systems that overcome the above-mentioned limitations and problems.

SUMMARY

Disclosed embodiments include an apparatus for water sampling and analysis, the apparatus comprising: (a) a device for water sampling at a plurality of depths comprising a hosepipe and a plurality of internal independent pipes with a plurality of sampling inlets at a plurality of water depths, and (b) a pumping system to pump a sample of water collected using the device for water sampling at a plurality of depths to an isolated module for analysis.

Disclosed embodiments include an autonomous multi-parametric buoy for multi-depth water sampling, monitoring, data collection, transmission, and analysis designed primarily to overcome the major limitations of current systems, namely, 1) the direct contact and immersion of the sensors in water requiring constant maintenance involving in-situ manual cleaning and re-calibrations, 2) the limited monitoring depth, 3) the limited number of sensors, 4) the limited power autonomy, and 5) the limited remote-control capabilities.

According to one particular embodiment, and without limitation, the apparatus for water sampling an analysis is implemented as a buoy which includes (a) a system for water sampling at a plurality of depths by means of a hosepipe comprising a plurality of independent pipes with sampling inlets at a plurality of water depths and a mechanic, hydrostatic, or pneumatic pumping system designed to pump the sampled water to an isolated reading module; (b) an isolated reading and analysis module designed to guarantee optimal environmental characteristics for a plurality of sensors capable of data analysis at a plurality of depths from a single isolated location; (c) a system for remote maintenance by means of a plurality of antifouling coatings and pre-programmed or remote-controlled sensor self-cleaning and self-calibration capabilities; (d) a plurality of renewable energy sources including a photovoltaic module, a wind module, and a wave module to provide stable and continuous power to the electronics systems controlling the smart monitoring buoy; and (e) a system for collecting, analyzing, storing samples, and transmitting monitoring data at pre-programmed time intervals or on-demand by means of two-way communications and remote control.

BRIEF DESCRIPTION OF THE DRAWINGS

Disclosed embodiments are illustrated by way of example, and not by way of limitation, in the figures of the accompanying drawings.

DETAILED DESCRIPTION

Figure 1:
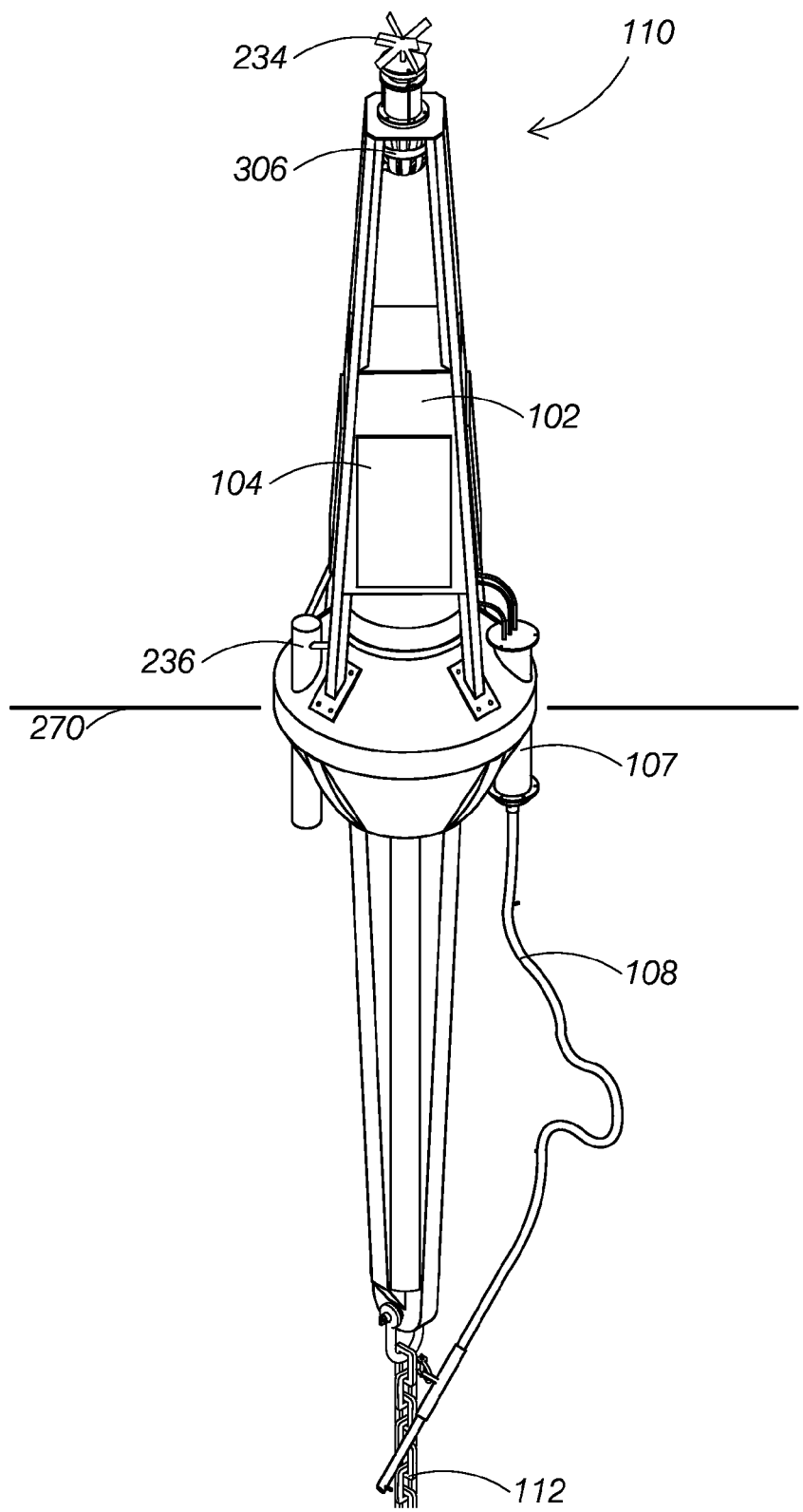
FIG. 1 shows an illustration of the smart monitoring buoy according to one embodiment and the most salient external structural elements.

Disclosed embodiments include apparatus and methods for sampling seawater and fresh-water characteristics involving remote-controlled smart multi-parametric buoys capable of self-maintenance, water sampling, monitoring, data collection, data transmission, and analysis. Embodiments of the autonomous multi-parametric buoy for water sampling, monitoring, data collection, transmission, and analysis are designed to overcome the major limitations of current systems, namely, 1) the direct contact and immersion of the sensors in water requiring constant maintenance involving in-situ manual cleaning and re-calibrations, 2) the limited monitoring depth, 3) the limited number of sensors, 4) the limited power autonomy, and 5) the limited remote-control capabilities.

Disclosed embodiments include an apparatus for water sampling and analysis, the apparatus comprising: (a) a device for water sampling at a plurality of depths comprising a hosepipe and a plurality of internal independent pipes with a plurality of sampling inlets at a plurality of water depths, and (b) a pumping system to pump a sample of water collected using the device for water sampling at a plurality of depths to an isolated module for analysis.

According to one particular embodiment, and without limitation, the buoy comprises (a) a system for water sampling at a plurality of depths by means of a hosepipe 108 comprising a plurality of internal independent pipes 220 with sampling inlets 126 at a plurality of water depths 222 and a mechanic, hydrostatic, or pneumatic pumping system 232 designed to pump the sampled water to an isolated reading module 106; (b) an isolated reading and analysis module 106 designed to guarantee optimal environmental characteristics for a plurality of sensors 230 capable of data analysis at a plurality of depths from a single isolated location; (c) a system for remote maintenance by means of a plurality of anti-fouling coatings and pre-programmed or remote-controlled sensor self-cleaning and self-calibration capabilities; (d) a plurality of renewable energy sources 300 including a photovoltaic module 104, a wind module 234, and a wave module 306 in order to provide stable, continuous, reliable, and diversified power to the electronics systems controlling the smart monitoring buoy; and (e) a system for collecting, analyzing, storing samples 116, and transmitting monitoring 119 data at pre-programmed time intervals or on-demand by means of two-way communications and remote control.

Figure 2:
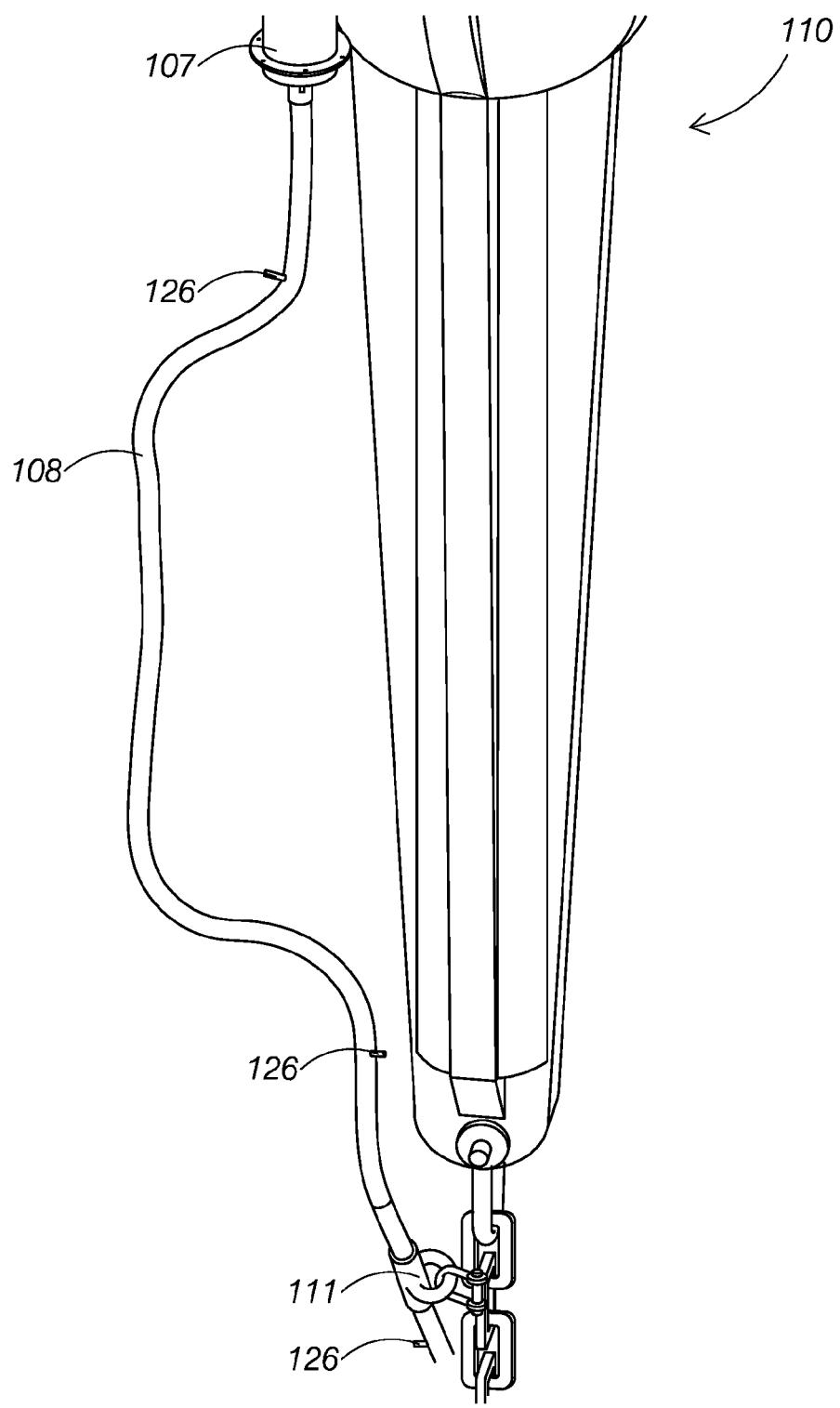
FIG. 2 shows an embodiment of the smart monitoring buoy illustrating the below-water components including the system for water sampling at a plurality of depths by means of a hosepipe comprising a plurality of independent pipes inside with sampling inlets at a plurality of water depths.
Figure 3:
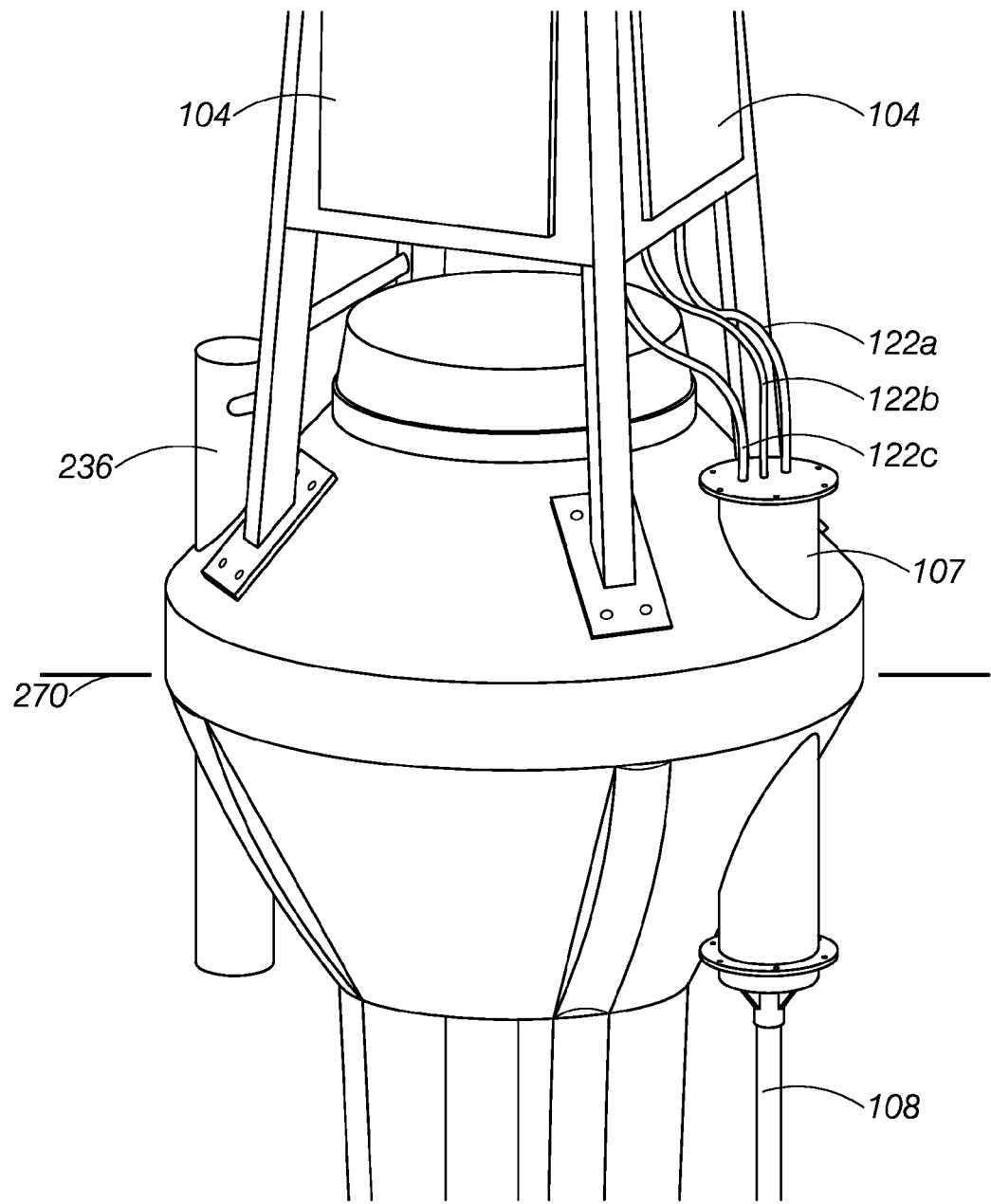
FIG. 3 shows an embodiment of the smart monitoring buoy illustrating the water-level components such as the support pipe, the photovoltaic collectors, and the buoy frame.

FIG. 1 shows an illustration of the smart monitoring buoy according to one embodiment and the most significant external structural elements. FIG. 2 shows an embodiment of the smart monitoring buoy illustrating the below-water components including the system for water sampling at a plurality of depths by means of a hosepipe comprising a plurality of independent pipes with sampling inlets at a plurality of water depths; and FIG. 3 shows an embodiment of the smart monitoring buoy illustrating the water-level components such as the support pipe, the photovoltaic collectors, and the buoy frame.

According to one embodiment the smart buoy includes the modules described on each of the sections below.

A.1 Hosepipe and Support Pipes According to One Embodiment.

FIG. 2 shows an embodiment of the smart monitoring buoy illustrating the below-water components the system for water sampling at a plurality of depths by means of a hosepipe comprising a plurality of internal independent pipes with sampling inlets at a plurality of water depths.

The system for water sampling at a plurality of depths is based on a of a hosepipe 108 comprising a plurality of internal independent pipes 220 with sampling inlets 126 at a plurality of water depths and a mechanic, hydrostatic, or pneumatic pumping system 232 designed to pump the sampled water to an isolated reading module 106.

According to one embodiment, a strengthen hosepipe 108 of sufficient diameter to accommodate the sampling pipes 220 is designed to guarantee the integrity of the sampling system even when the buoy and its anchor train 112 undergo severe water and meteorological conditions.

The strengthen hosepipe 108 includes a plurality of metallic anchors 111 that serve as union points with the buoy and the anchor chain 112. The internal independent sampling pipes 220 contain external inlets though a hole in the hosepipe 108 at each depth where a sampling process is desired. The end 126 of each sampling pipe 220 is protected with a grid/filter in order to prevent solid materials entering into the water circuit. A copper pipe holds on the hosepipe in order to allow water sampling at each point and helps prevent obstructions in the sampling pipes 220. The hosepipe, the grids, as well as the filters are treated with antifouling products and coatings.

The upper part of the hosepipe 108 is firmly attached to the support pipe 107 and to the anchor train 112. It is inserted into the reading compartment 106 by means of metallic cases. The hosepipe 108 can be loose or firmly attached to the anchor chain 112.

When measures such as like temperature are sensitive to the sampling system, the required sensor is inserted in each of the capture points rising up the connecting wires (supply/data) by the inside of the hosepipe 108 and in parallel with the sampling pipes 220 to the surface where they are connected as in the case of other sensors.

According to one embodiment, the support pipe 107 is fitted to the rubber ring of the buoy, and it is intended to protect the reading compartment 106. It allows the hosepipe connection 108 in its lower part. Furthermore it allows for access and installation to the reading compartment 106 from the upper part for maintenance and repairing tasks.

A.2 Electrovalves According to One Embodiment.

Figure 4:
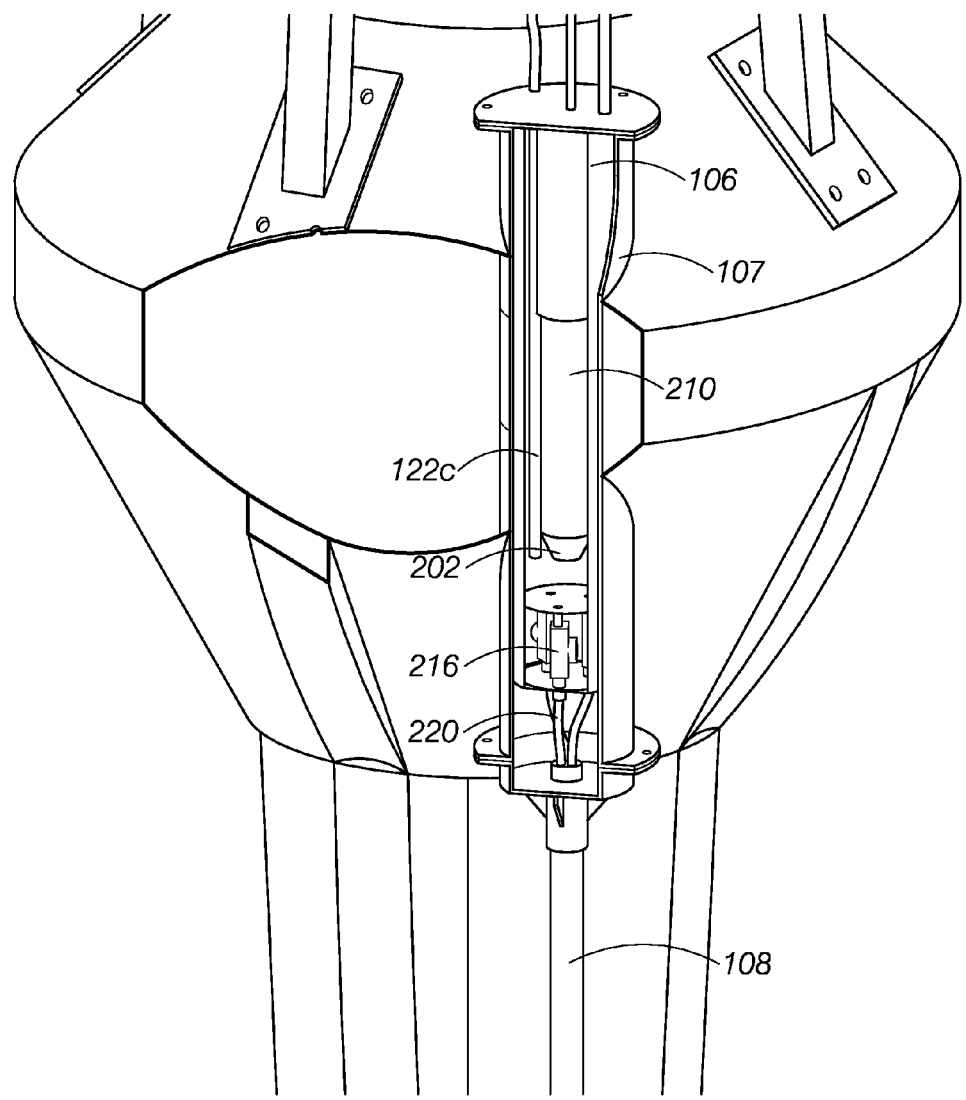
FIG. 4 shows an embodiment of the smart monitoring buoy illustrating the water-level components such as the reading compartment.

FIG. 4 shows an embodiment of the smart monitoring buoy illustrating the water-level components such as the reading compartment 106, the hosepipe 118, and the sampling pipes 220. The electrovalves compartment 214 is capable of accommodating as many sampling pipes 220 as included in the hosepipe 108.

Figure 8:
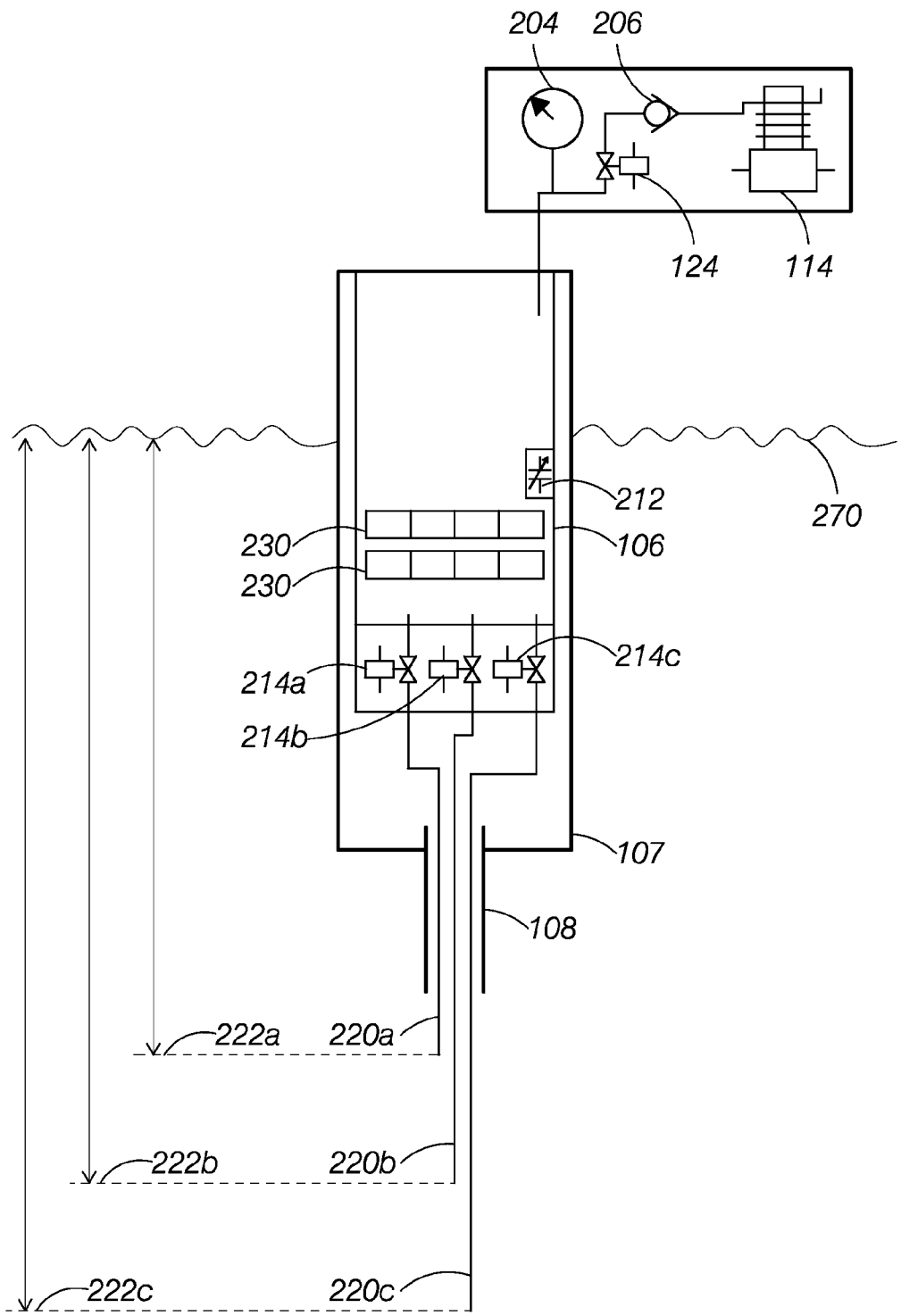
FIG. 8 shows a schematic diagram of keys features of the buoy according to one embodiment.
Figure 9:
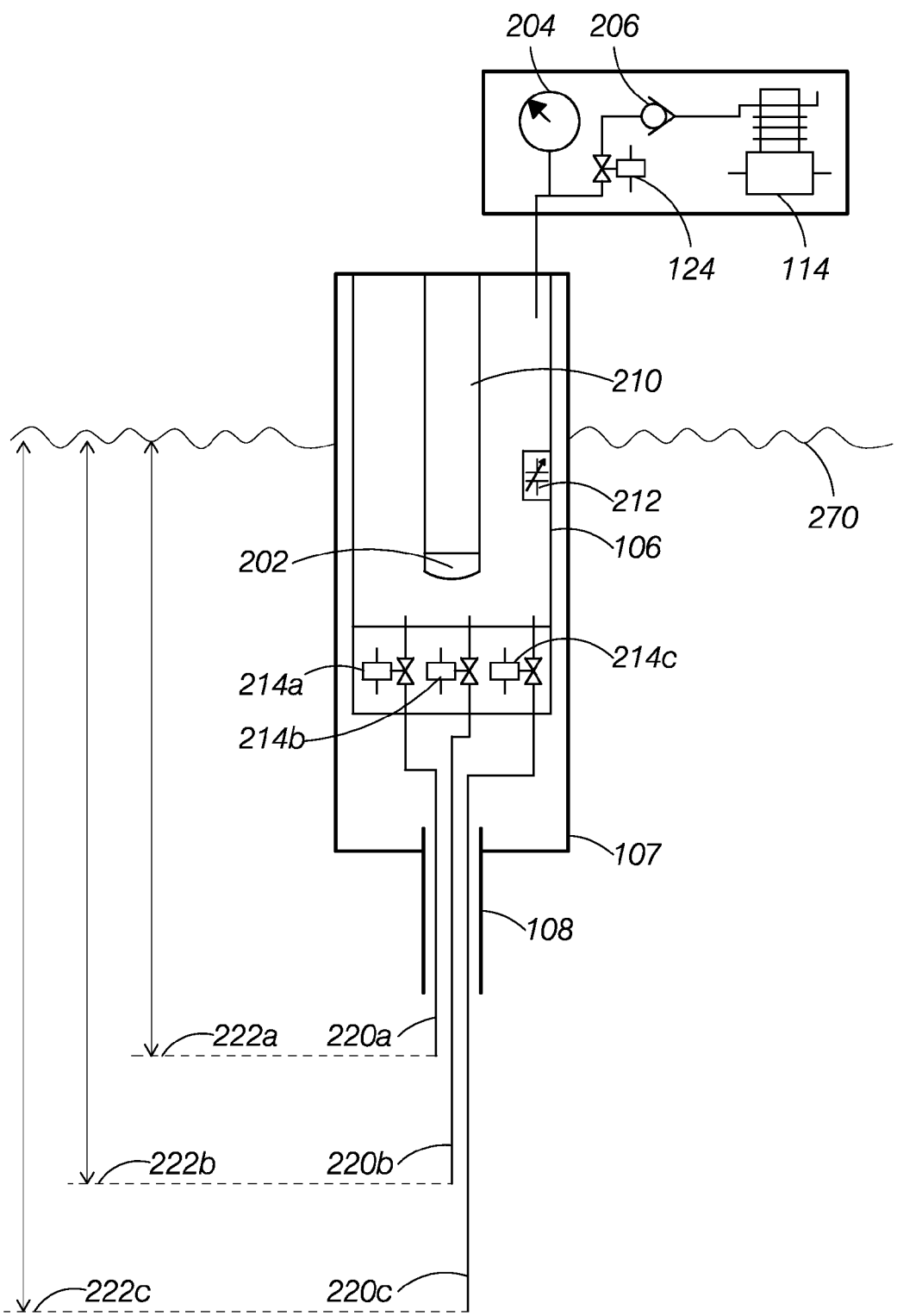
FIG. 9 shows a schematic diagram of key features of the buoy according to an alternative embodiment.
Figure 18:
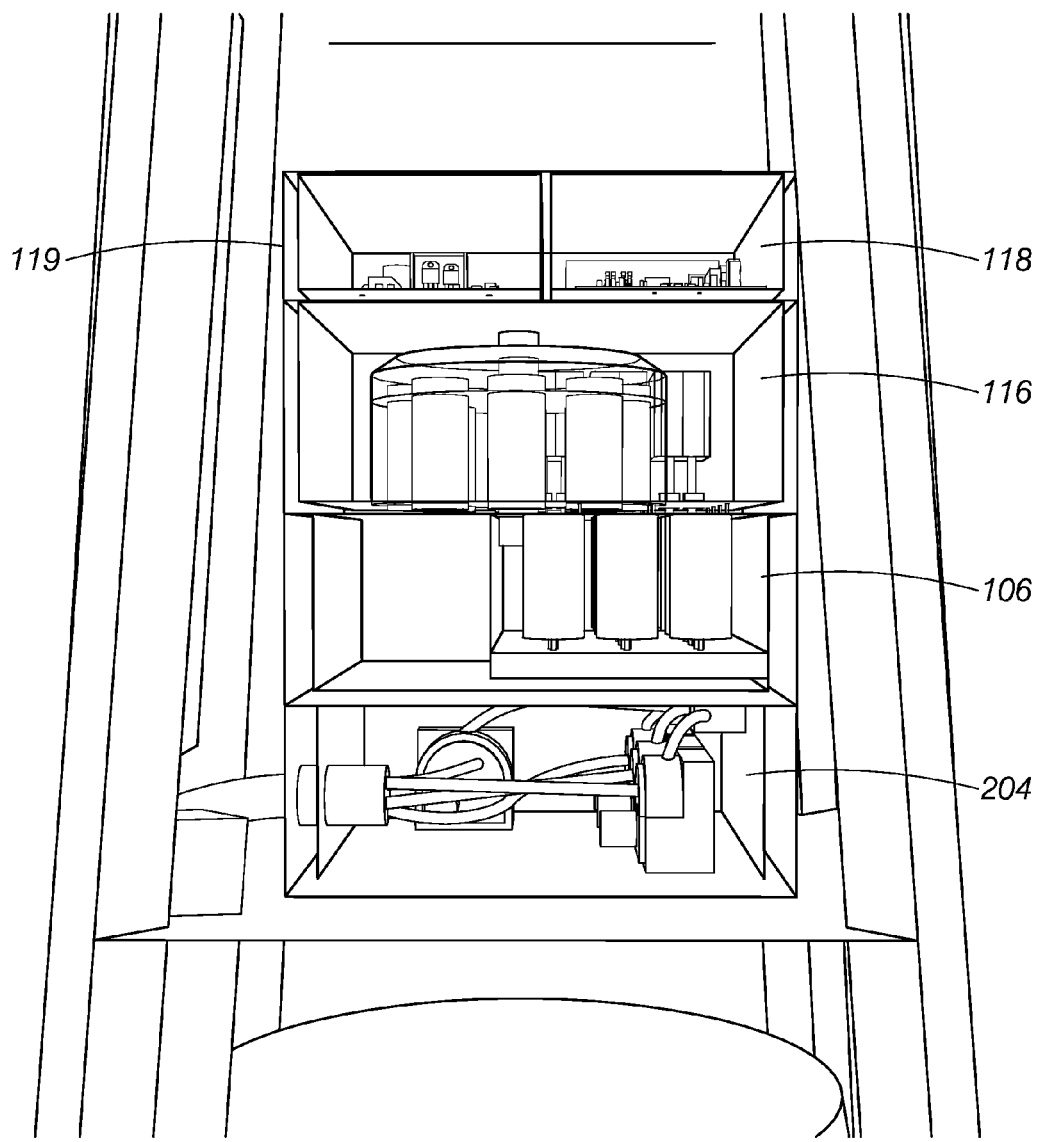
FIG. 18 shows an illustration of above-water internal compartments.
Figure 19:
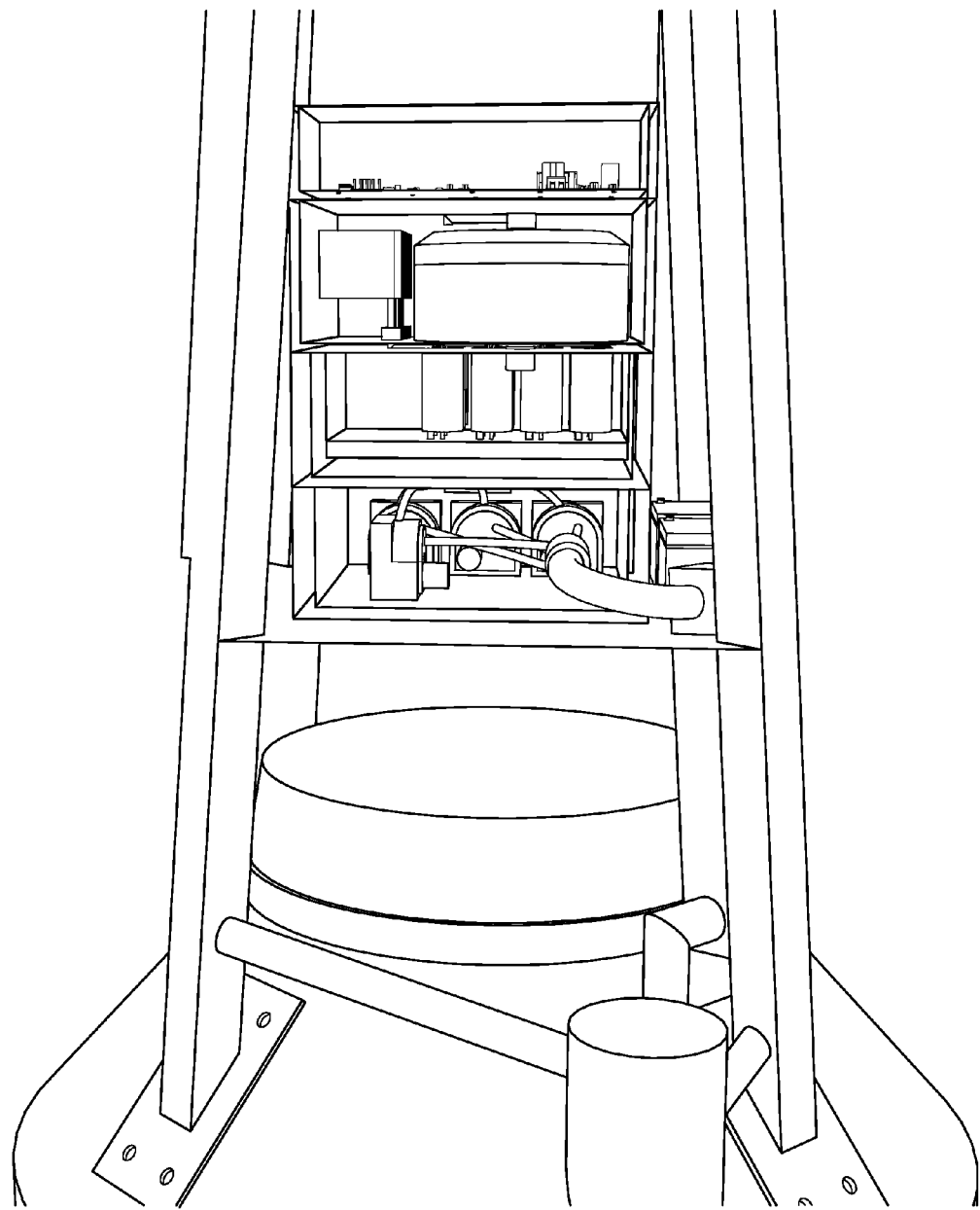
FIG. 19 shows an illustration of above-water internal compartments including the sample storage system.
Figure 20:
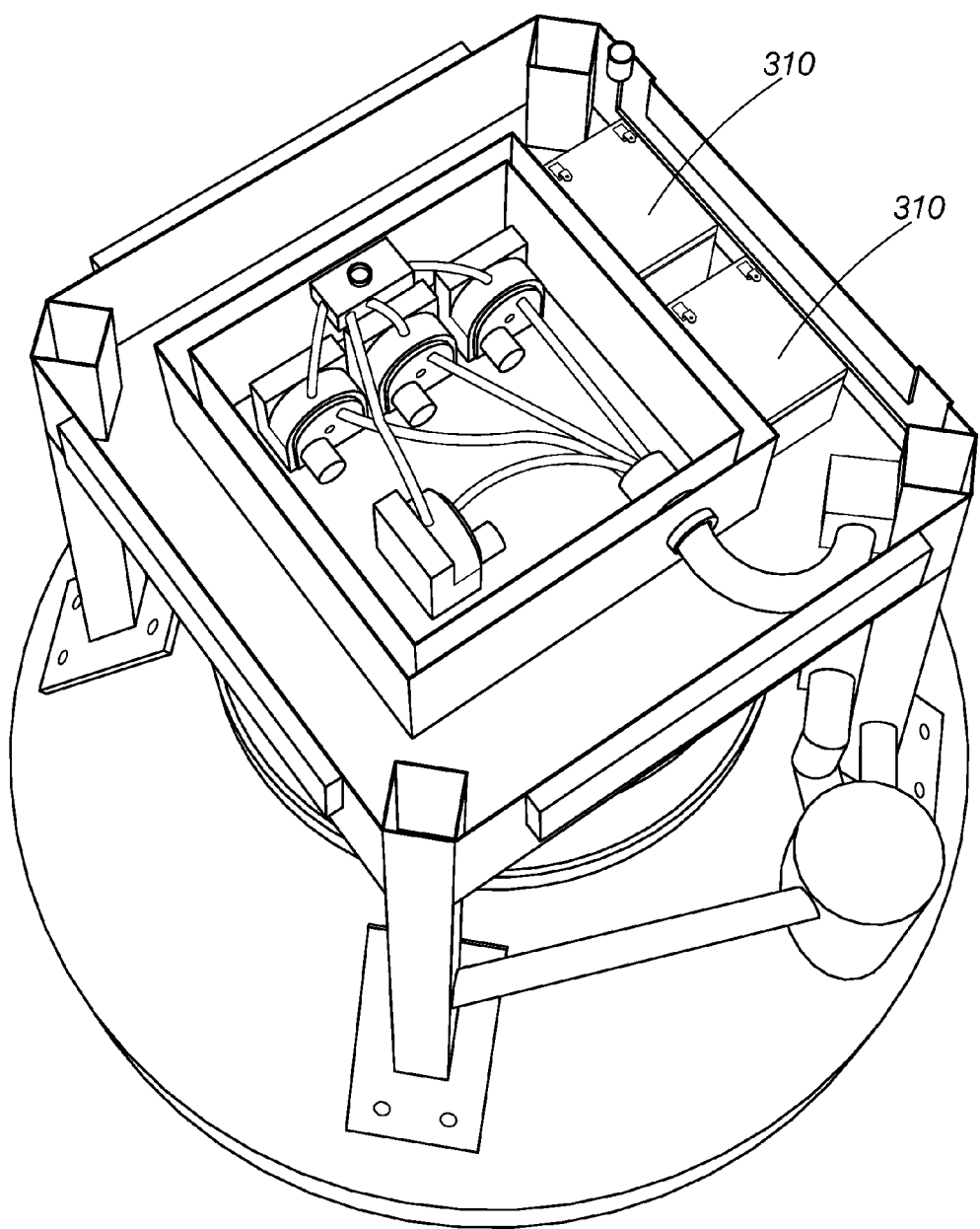
FIG. 20 shows an illustration of above-water internal compartments including a plurality of pipes.

Each sampling pipe 220 and depth have a corresponding electrovalve responsible for opening and closing the sampling pipe 108. This electrovalves compartment 214 is located under the water surface, right under the sensors cells 230, in order for the hydrostatic pressure to conduct the water to the sensors over the electrovalves. This structure is illustrated in FIG. 8, FIG. 9, and FIG. 18.

According to one embodiment, the emptying electrovalve 124 is located inside the buoy frame box 102 and allows for the pressure to equalize with the outside environment, freeing accumulated air in whole the circuit by means of the hydrostatic pressure. This operation results in the flooding in the sensors 202 or 230 (i.e. complete water immersion of the sensors in the sampled water to be analyzed). When it opens, it results in the filling of the reading compartment and the remainder of the circuit. Conversely, in its closed position it provokes the circuit to empty due to the injected compressed air from the compressor 114. This electrovalve 124 can be located above seawater level 270 since water never has to reach higher. All the electrovalves are controlled based on a microcontroller 258 located in the control module 118.

A.3 Pumps According to One Embodiment.

Figure 10:
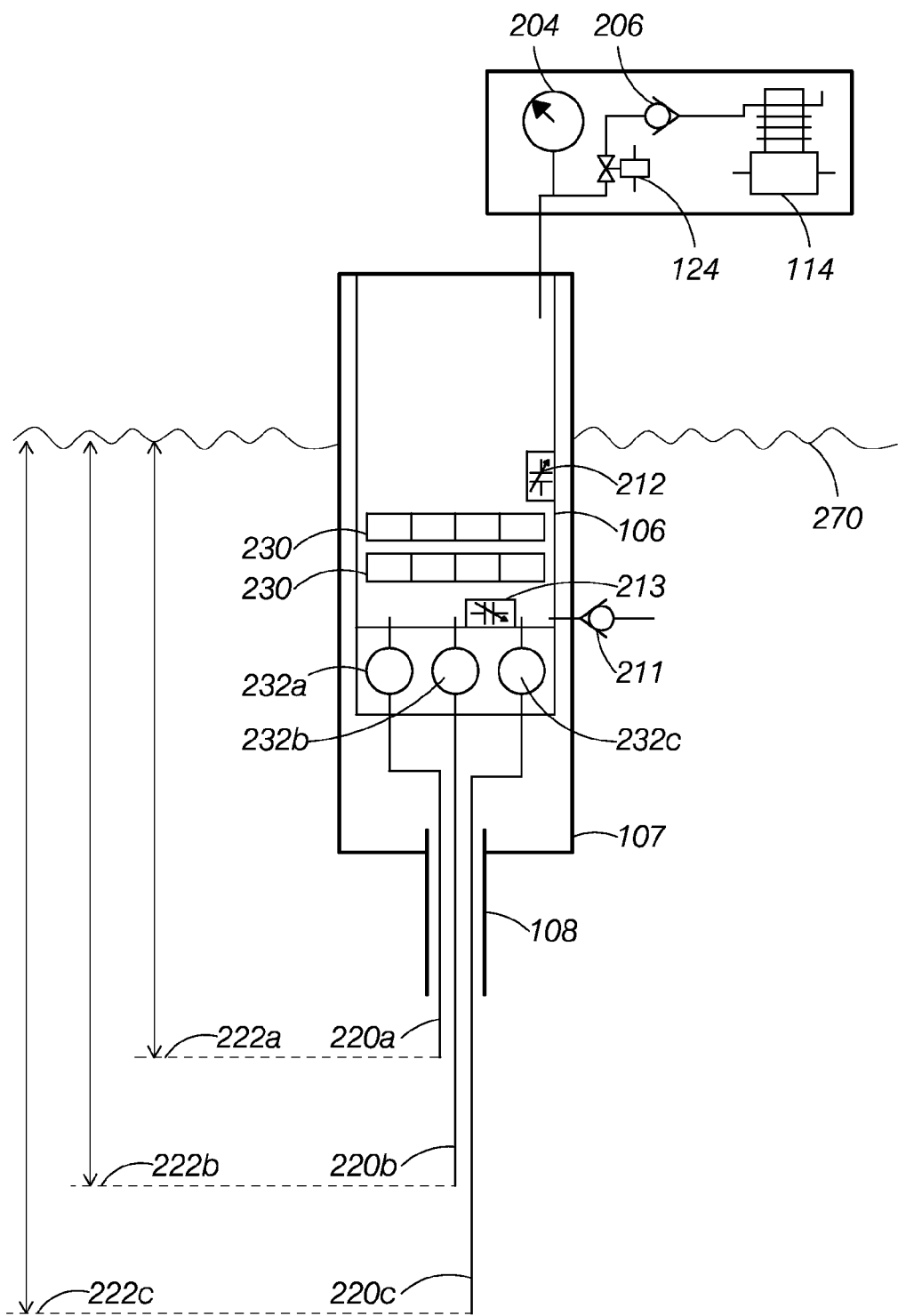
FIG. 10 shows a schematic diagram of key features of the buoy according to an alternative embodiment.
Figure 11:
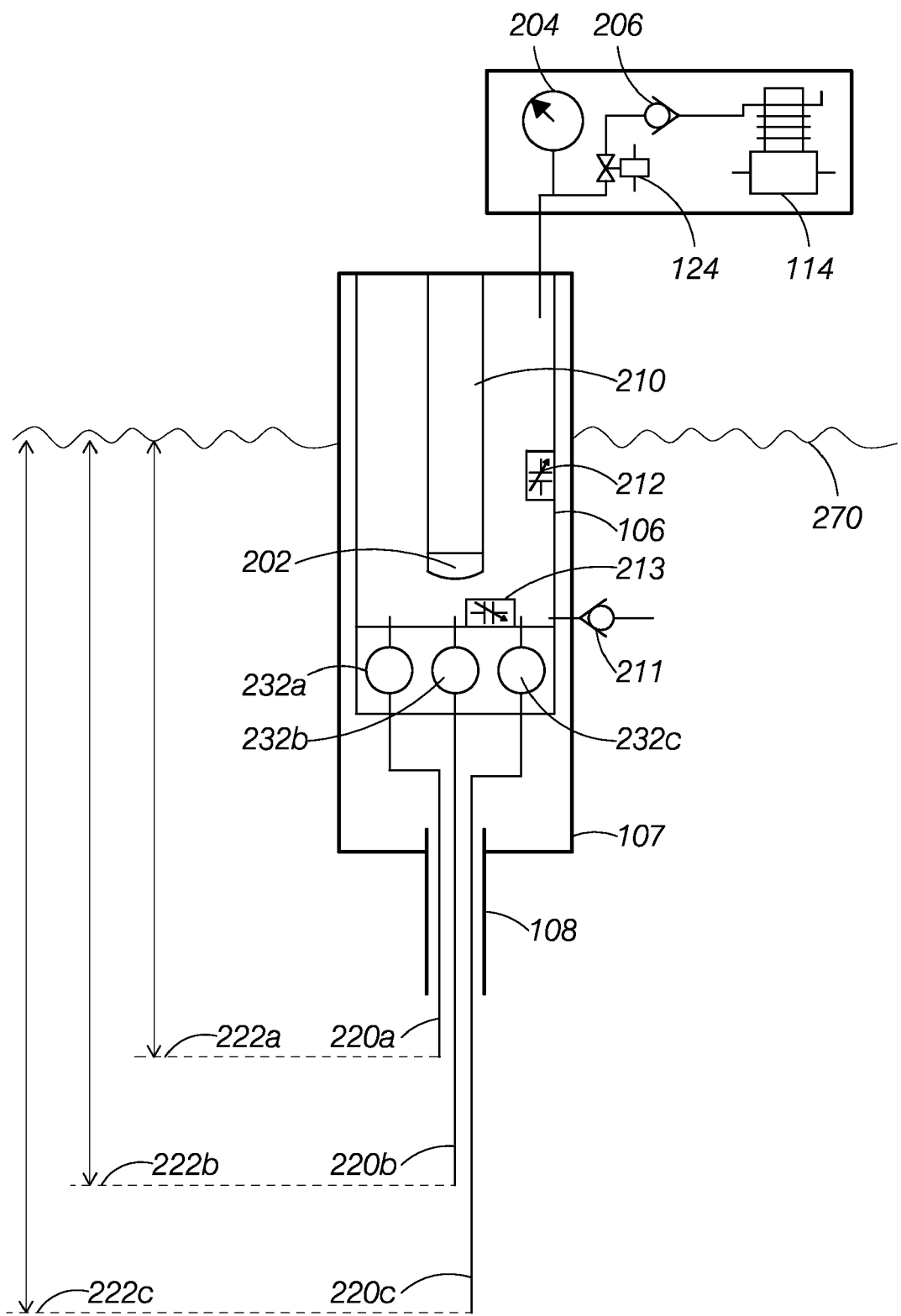
FIG. 11 shows a schematic diagram of key features of the buoy according to an alternative embodiment.
Figure 12:
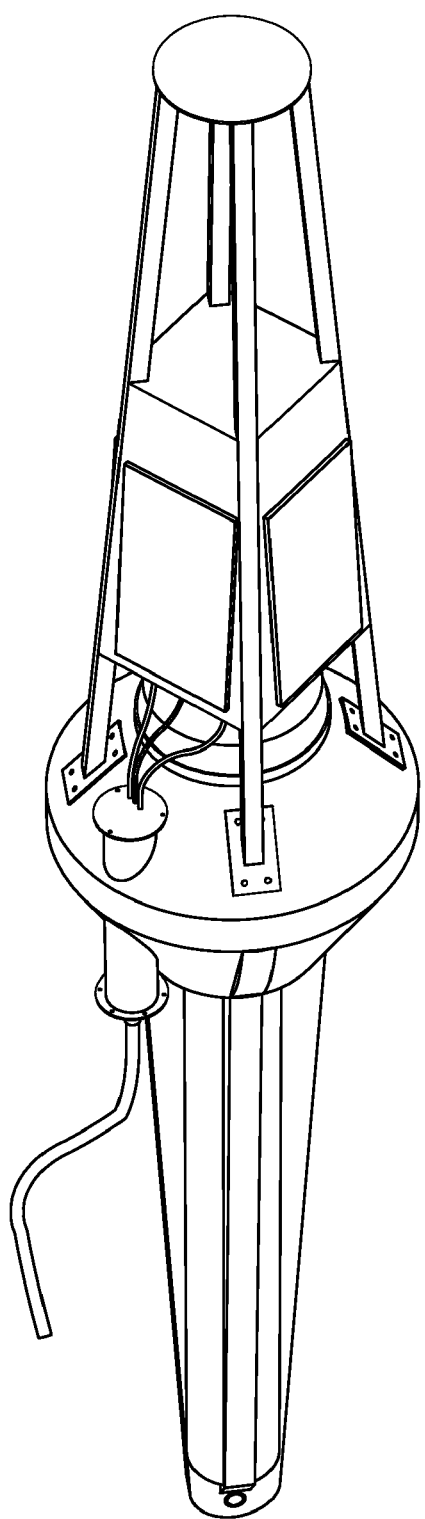
FIG. 12 shows a perspective view to illustrate the external design of the buoy according to one embodiment.
Figure 13:
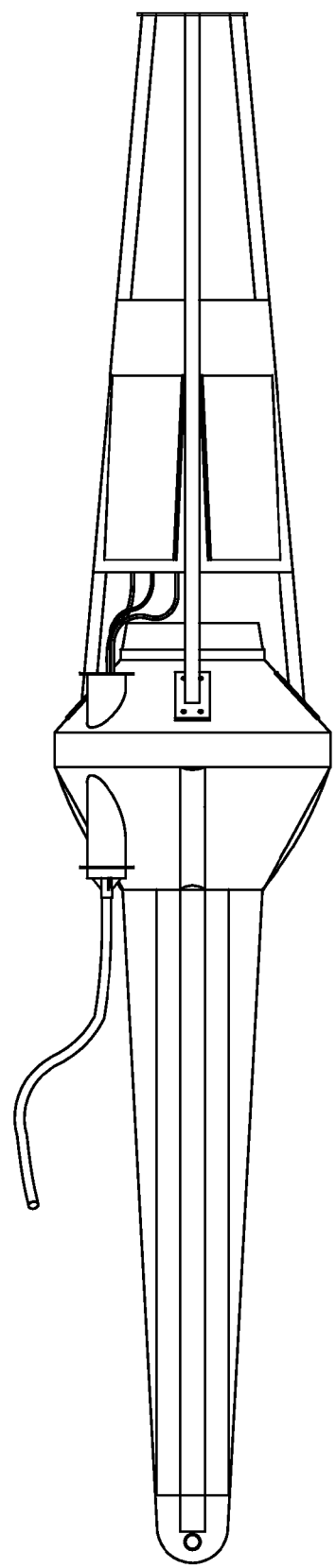
FIG. 13 shows a side view to illustrate the external design of the buoy according to one embodiment.
Figure 14:
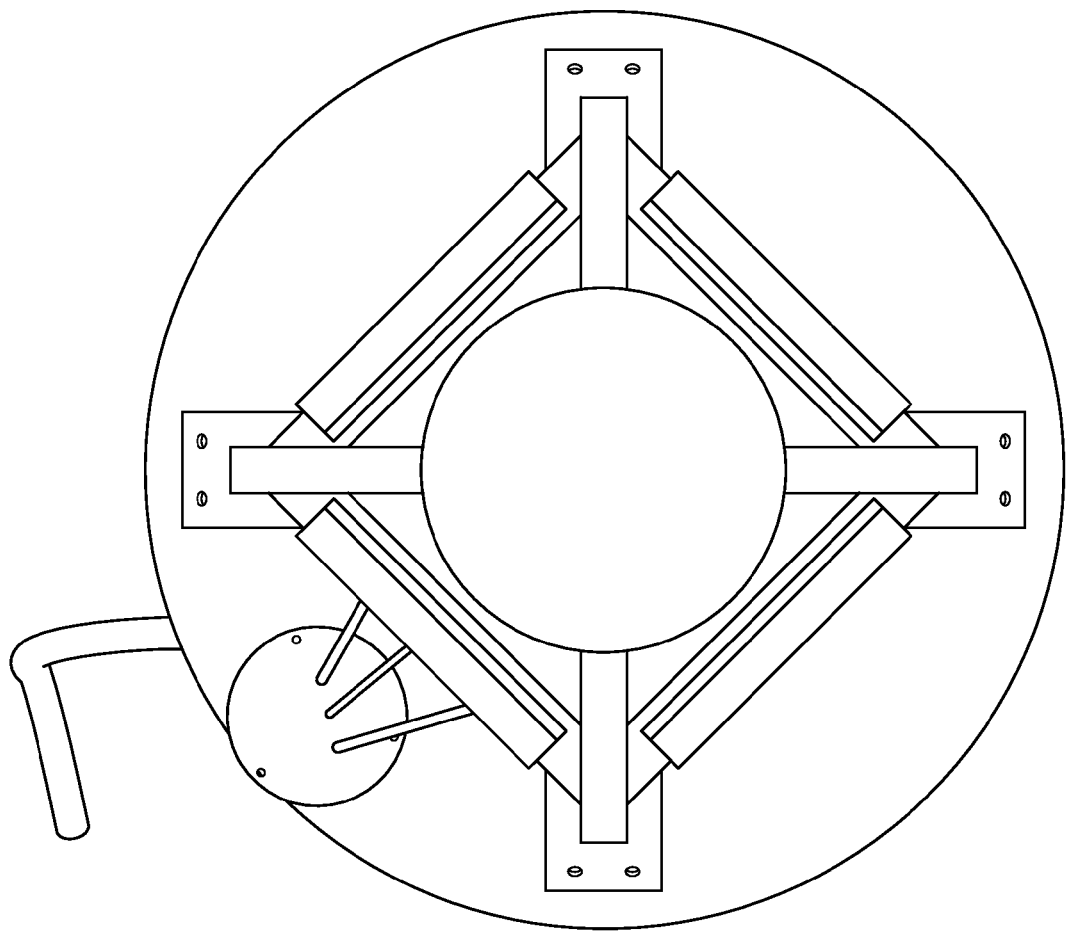
FIG. 14 shows a top view to illustrate the external design of the buoy according to one embodiment.
Figure 15:
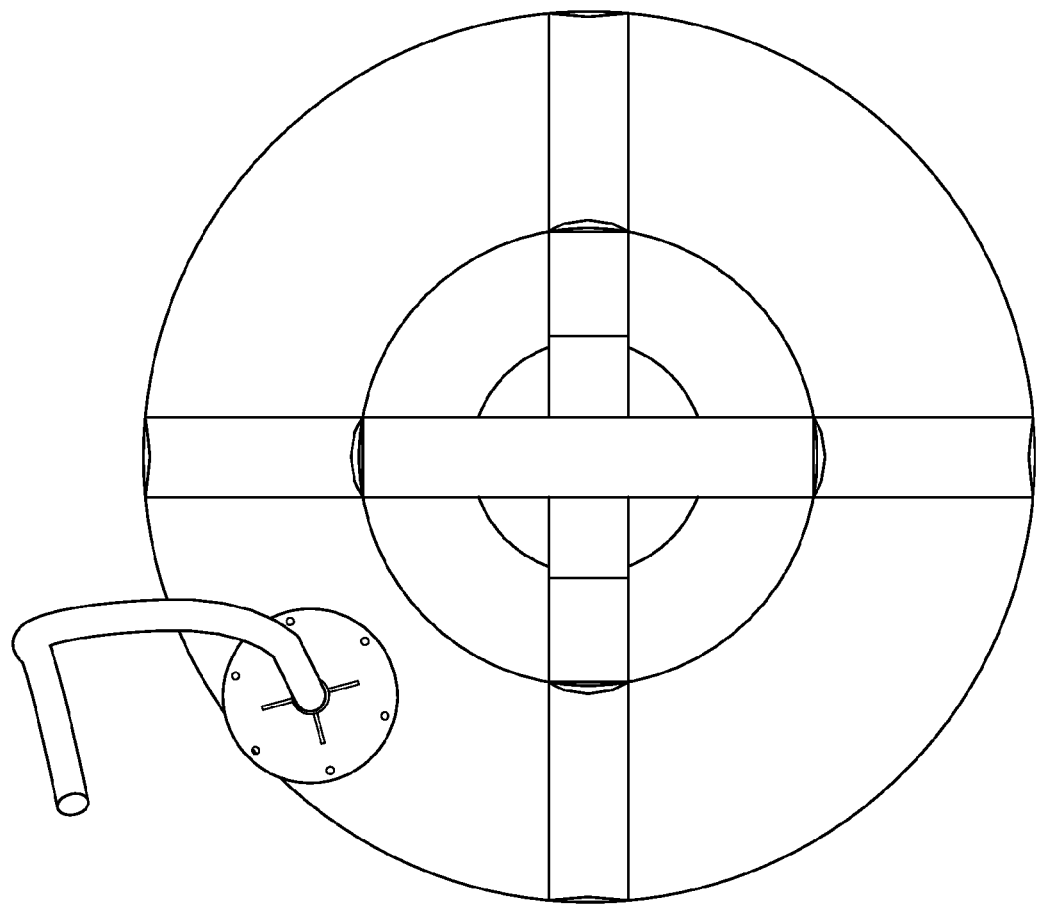
FIG. 15 shows a bottom view to illustrate the external design of the buoy according to one embodiment.
Figure 16:
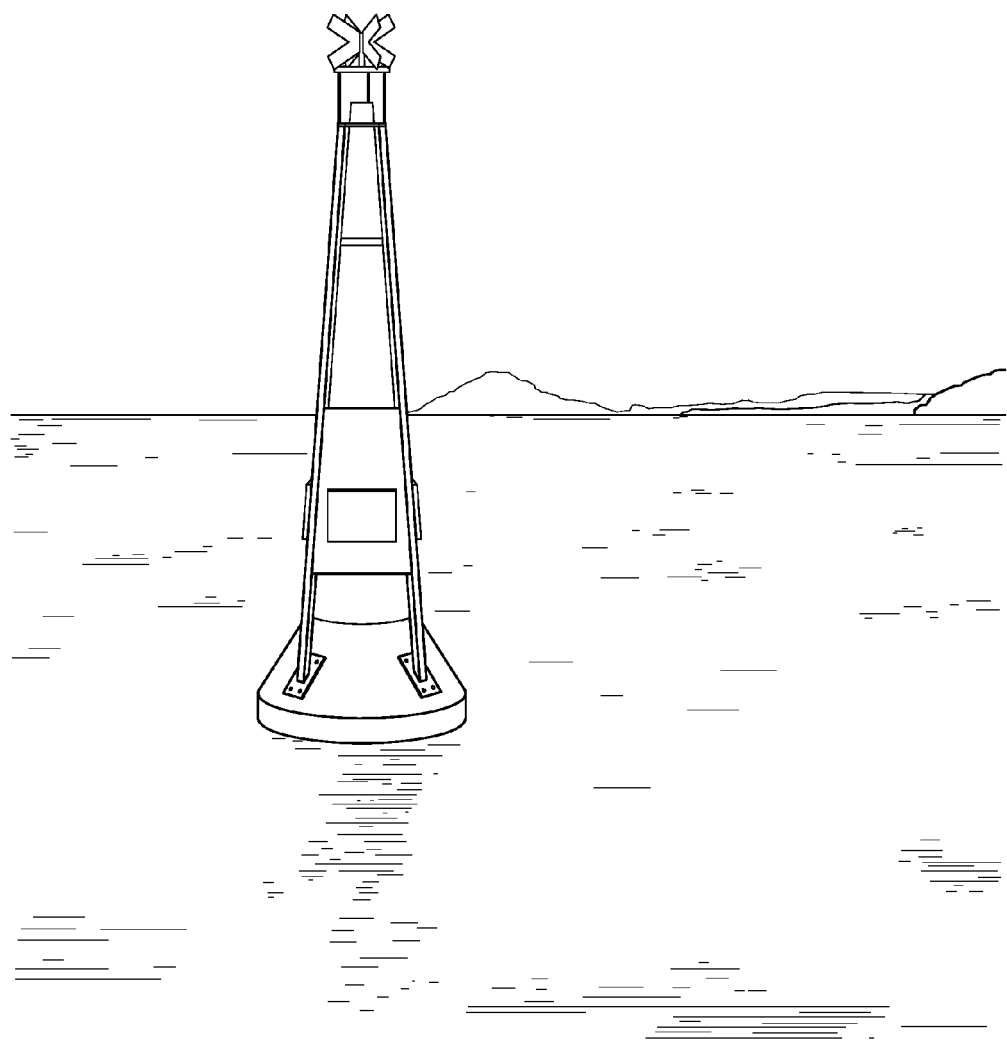
FIG. 16 shows a prototype of the smart buoy according to one embodiment.
Figure 17:
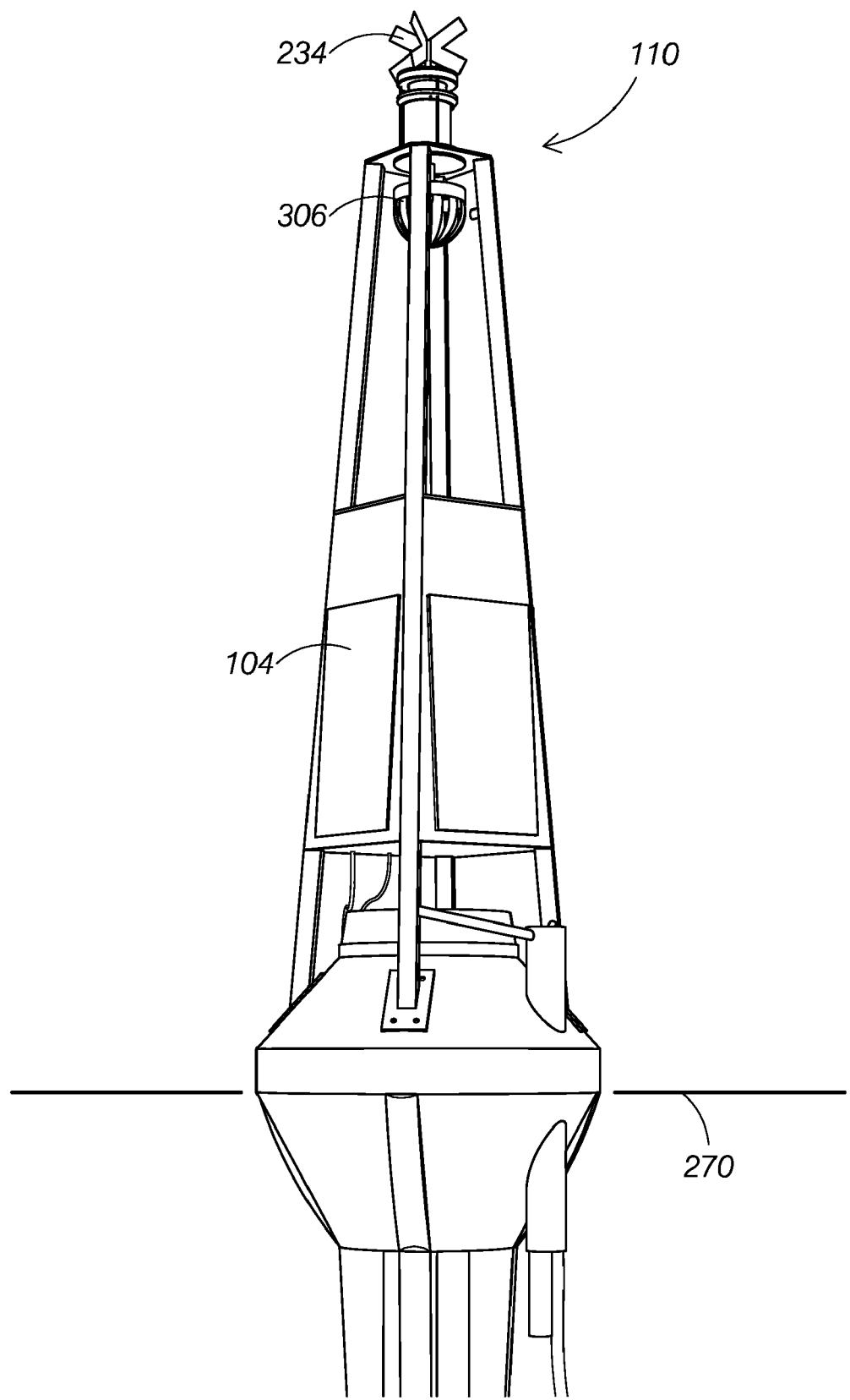
FIG. 17 shows an illustration of the buoy including its wind and photovoltaic modules.

FIG. 10 and FIG. 11 show a schematic diagram including the location and connection of the pumps 232a, 232b, and 232c. The plurality of pumps are designed to force the circulation of the water from the sampling point 126 to the reading compartment 106 through the sampling pipes 220. The pumping system can be mechanical, hydrostatic or pneumatic.

These pumps must have the special specification that they cannot change or contaminate the water they help move, since this water needs to be analyzed. According to one embodiment they are based on a peristaltic pump mechanism, membrane based or substantially equivalent. The pumps 232 are DC powered and are controlled based on a microcontroller 258 located in the control module 118. The number of pumps is a function of the number of sampling pipes corresponding to the number of depths the specific embodiment of the buoy is designed to monitor (e.g. 220a, 220b, and 220c will require three pumps).

A.4 Reading and Analysis Compartment According to One Embodiment.

FIG. 4 shows an embodiment of the smart monitoring buoy illustrating the water-level components such as the reading compartment 106.

Figure 5:
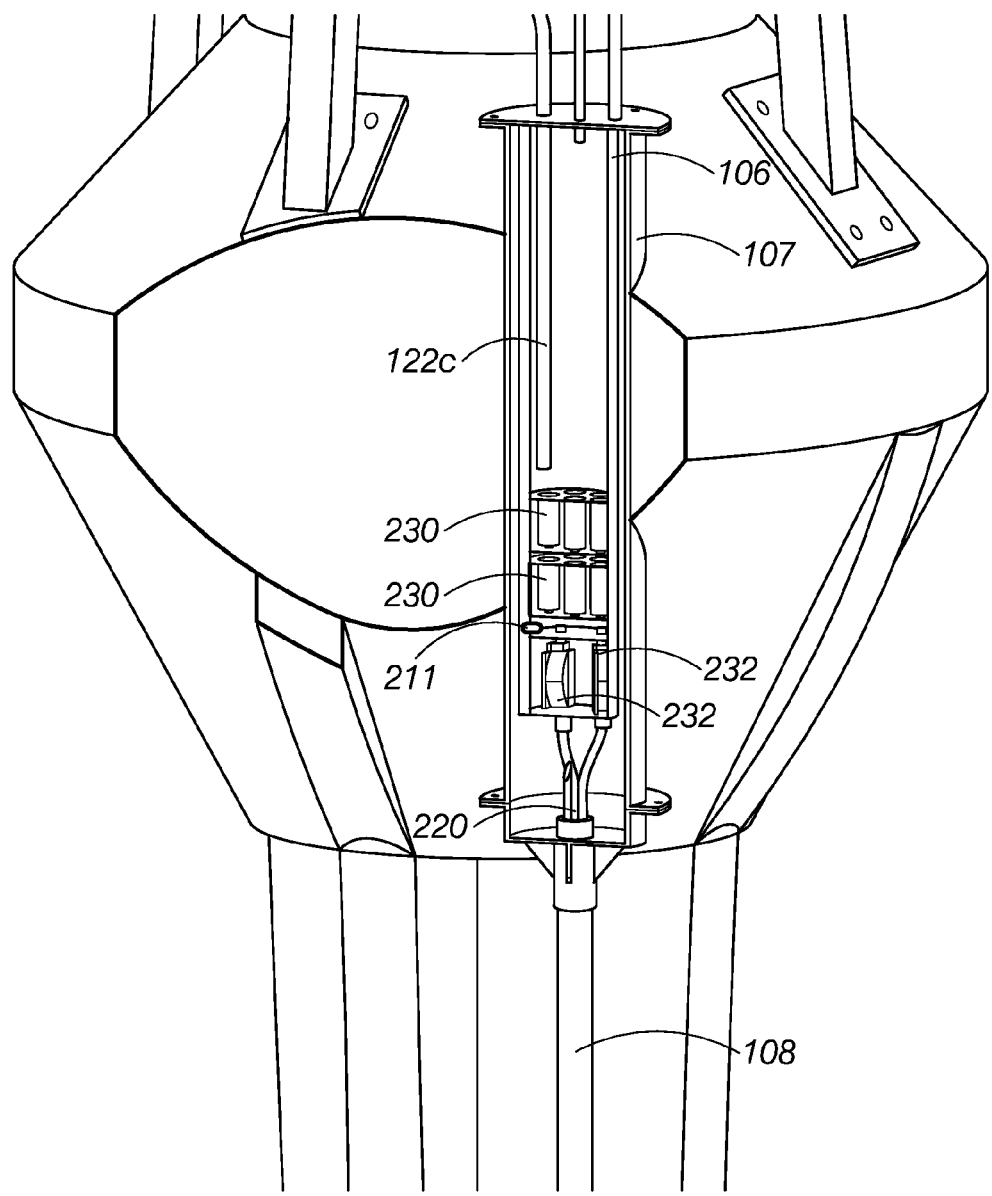
FIG. 5 shows an embodiment of the smart monitoring buoy illustrating a cross-section of the reading compartment.
Figure 6:
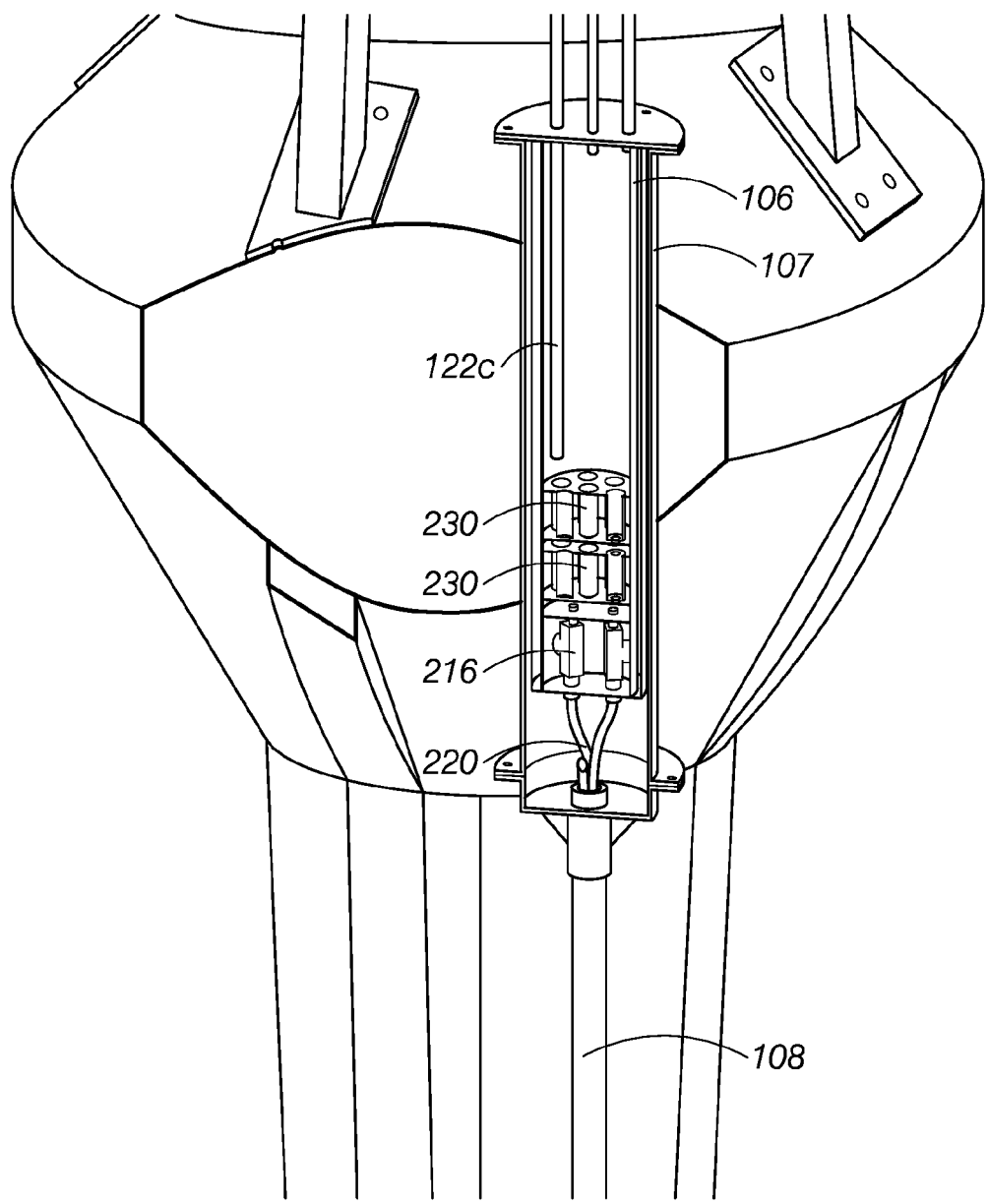
FIG. 6 shows an embodiment of the smart monitoring buoy illustrating a second cross-section of the reading compartment.

FIG. 5 and FIG. 6 show an embodiments of the smart monitoring buoy illustrating a cross-sections of the reading compartment 106. The reading or analysis compartment 106 is comprised of three parts (a) a bottom compartment including the electrovalves 214 or the pumps 232; (b) a middle compartment housing a plurality of sensors 230 and designed to maintain optimal environmental conditions for their isolation, protection, and optimal reading conditions; and (c) a top compartment to dispense non-valid water to be excluded from the analysis.

The reading compartment 106 is capable of accommodating most sensors currently available in the market. Additionally, these sensors can be incorporated either individually (standaloned) or as part of a multiparametric sensing system.

The interior surface of the reading compartment 106 is made by special materials and treated against or covered by antifouling materials.

FIG. 10 and FIG. 11 show a schematic diagram including the location and connections of the reading compartment 106. The reading compartment 106 works by selective action of the compressor 114 and the electrovalves 230 or the peristaltic pumps 232 that allows water filling or emptying of the circuit corresponding to each independent sampling pipe 220. This operation is equivalent to reading a sample in the desired water depth, even though the sensors are maintained in isolation at a secured and environmentally safe compartment. The manometer 128 measures the pressure and the water level sensor 212 enables for the control of water filling and emptying. The pressure is stabilized when the circuit frees air by its lower part at the sampling point as well as giving information about the sampling water depth. Upon pressure stabilization the valve corresponding to the sampling tube under analysis is closed and the compressor 114 is stopped. This is a novel method of multi-depth reading by means of a hosepipe 108 comprising a plurality of independent pipes 220 with sampling inlets 126 at a plurality of water depths and a mechanic, hydrostatic, or pneumatic pumping system 232 designed to pump the sampled water to an isolated reading module 106 and an isolated reading and analysis module 106 designed to guarantee optimal environmental characteristics for a plurality of sensors 230 capable of data analysis at a plurality of depths from a single isolated location is controlled based on a microcontroller 258 located in the control module 118.

A.5 Compressor According to One Embodiment.

Figure 7:
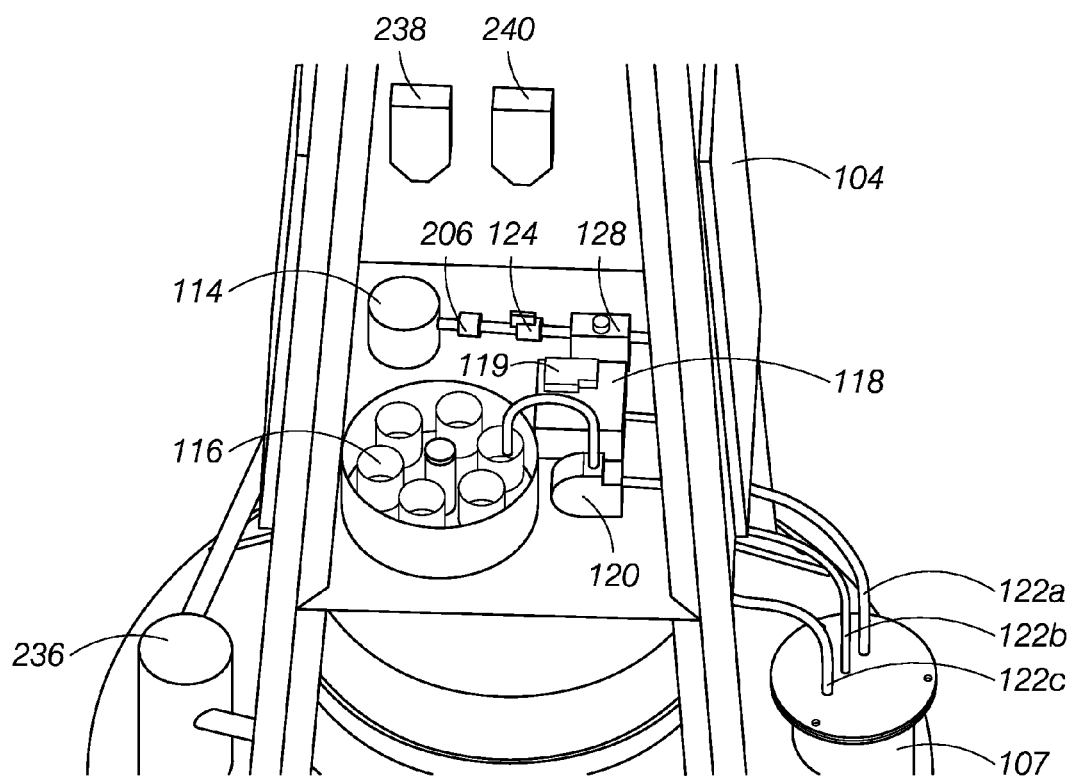
FIG. 7 shows an embodiment of the smart monitoring buoy illustrating a cross-section of above-water components including the compressor, pumps, and sample storage compartments.

FIG. 7 shows an embodiment of the smart monitoring buoy illustrating a cross-section of above-water components including the connection and location of the compressor 114, special pump 220, and sample storage compartments 116.

The compressor 114 is controlled by an electric engine supplied by the batteries 310 and managed by the control module 118. The compressor is designed to be capable of supplying air with a pressure equal to the necessary bars corresponding to the highest sampling depth necessary. According to one embodiment, and without limitation, the compressor is selected to be capable of supplying the necessary bars for depths over 100 m. This guarantees that the generated pressure is adequate of emptying the sampling pipe 220 at the highest water sampling depth.

According to one embodiment, the compressor 114 is located inside the buoy frame box 102, above the water surface. A pressure hosepipe with an antireturn valve 206 injects air into the reading compartment 106 as long as the emptying electrovalve 124 is closed and the sampling pipe 220 valve is opened. This forces the water circuit to empty. When the manometer pressure is fully stabilized this indicates the water circuit is fully emptied causing the closing of the valve in the sampling tube 220 as well as turning off the compressor 114. Additionally, this operation enables the buoys to determine the sampling depth as redundancy and checking mechanism. This operation is controlled based on a microcontroller 258 located in the control module 118.

A.6 Control Module According to One Embodiment

Figure 21:
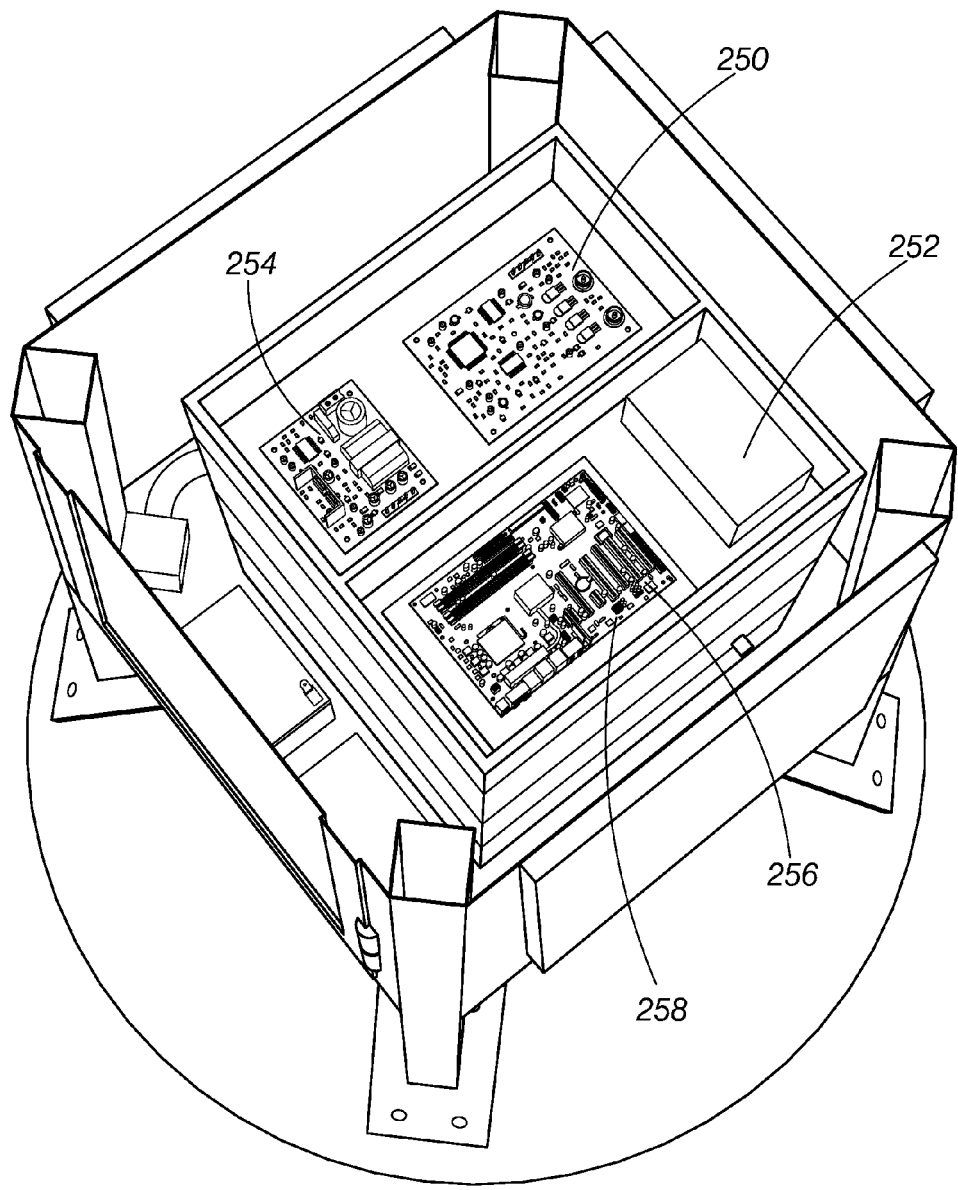
FIG. 21 shows an illustration including the electronics, controls, datalogging, positioning, and communication systems.
Figure 22:
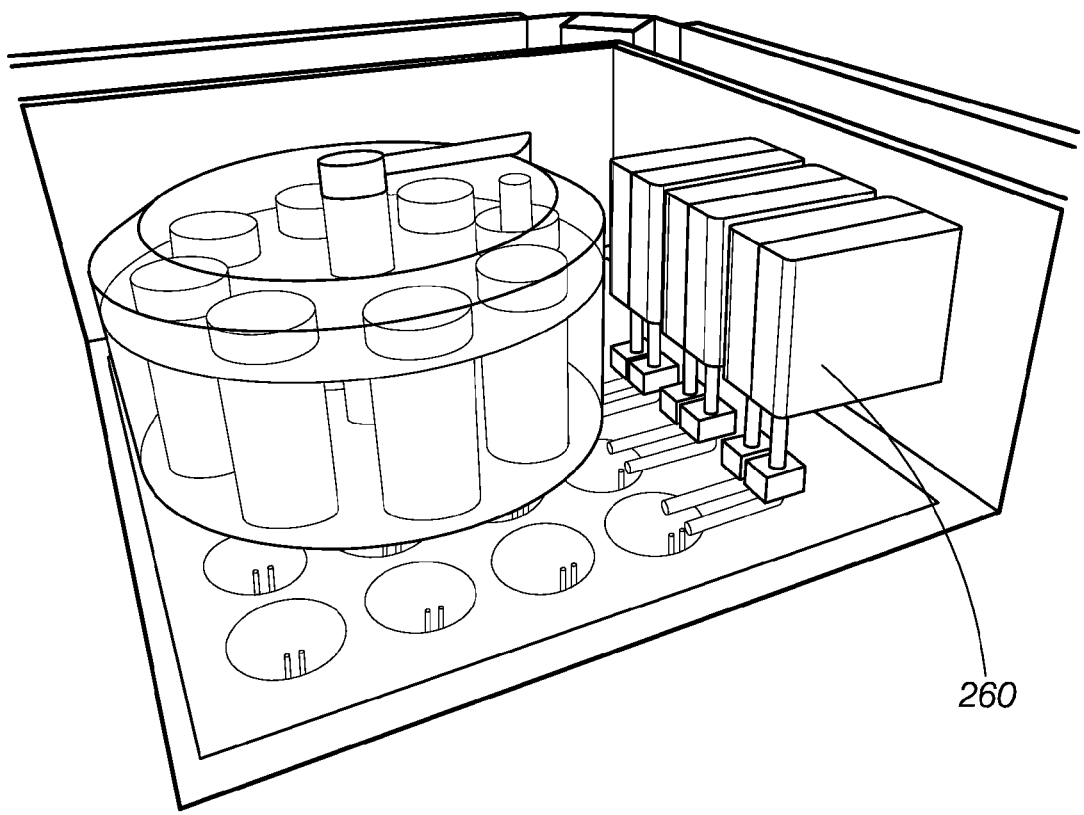
FIG. 22 shows an illustration of the system of self-calibration including the compartments containing the plurality of calibration liquids.

FIG. 18 shows the location of the control module. The control module 118 has the necessary software and hardware in order to control the operation all the systems comprising the buoy. Control of the system functions is achieved by means of standard microcontroller control means. FIG. 21 shows a graphical representation illustrating the location of the microcontroller 258 and the memory data storage 256.

According to one embodiment, the control module 118 has the capacity to support control operations for meteorological sensors 322, water analysis sensors, and inertial sensors as well as control the correct function of the supply circuits, detect system failures and malfunctions, and alter sampling cycles as a function of batteries charge level.

The main functions of the control module 118 are:
Managing the multi-depth water sampling process in order to enable for reading/analysis by the sensors 202 or 230. In order to accomplish this task, the control module 118 controls the electrovalves 214 responsible for closing or opening the passage of fluids, as well as the compressor 114 in order to turn it on and off to accomplish multi-depth water sampling (collection) and reading (analysis). Additionally, it comprises also a manometer 204 that the control module samples in order to control the pressure in the sampling pipes 220 and a water level sensor 212 to detect the presence of water at the appropriate level in order to cover the sensors 202 or 230.

Managing the activation and control of the sensors the sensors 202 or 230 in order to determine the reading order of said sensors, as well as storing the analyzed samples with a water depth tag corresponding to the depth of the sampled and analyzed water in a datalogger 250 as well as sending this data to the communication module for transmission to the central server.

Managing and controlling the reception of remote orders in order to modify the sampling algorithm (e.g. sampling frequency, depths, etc), as well as controlling the self-cleaning and self-calibration of the sensors. Additionally, it controls the capture of buoy parameters including energy levels, datalogger free memory space, malfunction detections, etc in order to notify the central server of these characteristics.

Figure 23:
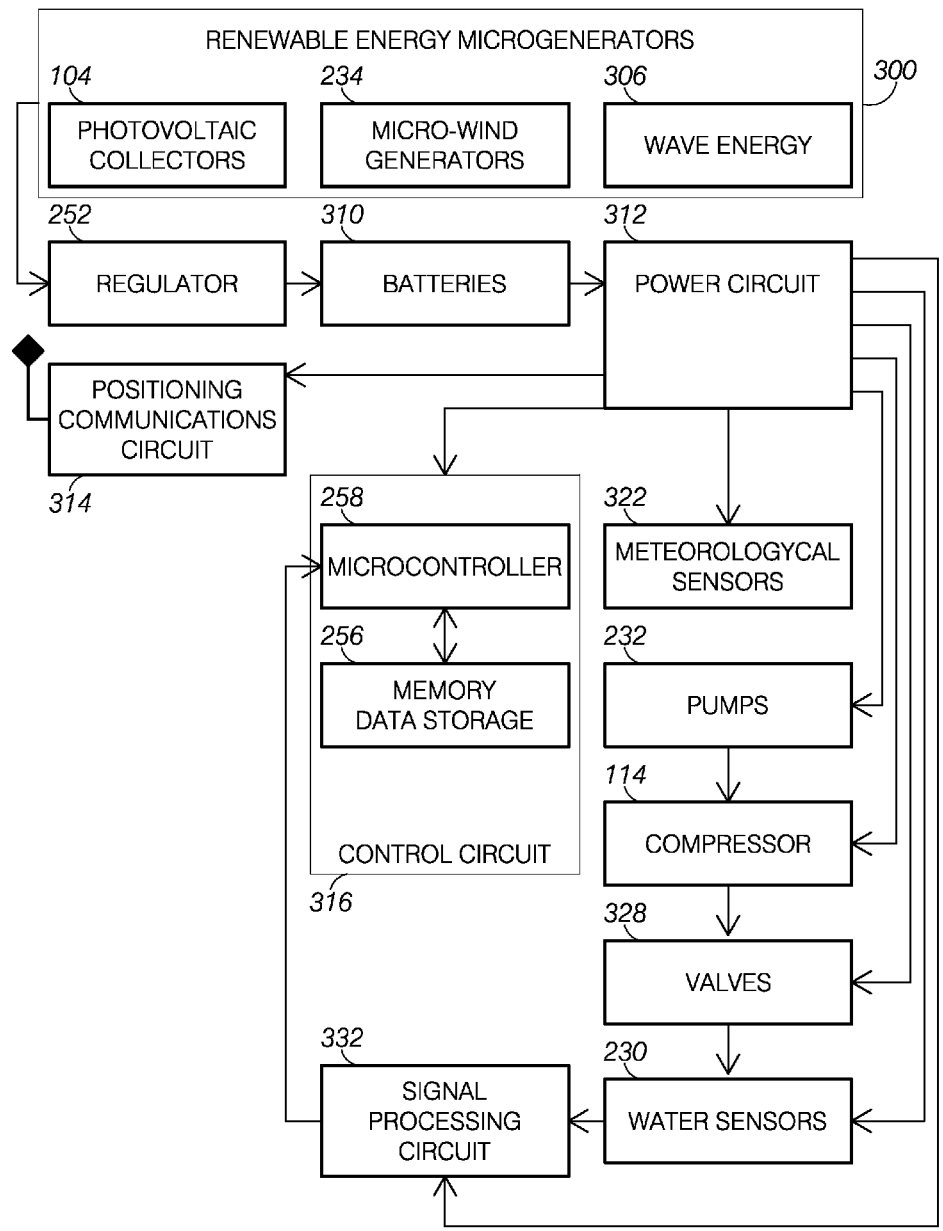
FIG. 23 shows a block diagram including the most significant electronics systems comprising the smart buoy.

FIG. 23 shows a block diagram illustrating the main electronic systems according to one embodiment of the buoy.

A.7 Communication Module According to One Embodiment.

Certain specific details are set forth in the following description and figures to provide a thorough understanding of various embodiments disclosed. Certain well-known details often associated with computing, communication, and software technology are not set forth in the following disclosure to avoid unnecessarily obscuring the various disclosed embodiments. Further, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc. that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

FIG. 18 shows the location of the communication module. The communication module 119 is responsible for receiving all the data captured by the control module 118, georeferencing these data, and transmitting them to the remote data collection server. Furthermore it can receive remote-controlled orders from that server and send them to the control module 118 to modify sampling patterns, cleaning sensors, calibrating sensors, etc.

This module communication module 119 includes digital and analog input and output, as well as a plurality of ports to interact with the control module (including RS232). It also has a satellite position receptor that can supply data through the serial port from the control unit and add a GPRMC NMEA sentence in order to georeference the data. Consequently, each data stream contains a station identifier which enables the receptor to determine the buoy of origin. Once all the data has been identified and georeferenced, according to one embodiment and without limitation, the communication module establishes a TCP/IP connection via GPRS or satellite with the server and transmits all the collected data. The buoy includes radio communications, satellite communications, GPRS, as well as GPS 254 positioning systems. Other similar and substantially equivalent protocols can also be used and incorporated. FIG. 23 illustrates a block diagram including the different electronics modules comprising the buoy according to one embodiment.

A.8 Acquisition Server Module According to One Embodiment.

The acquisition server module is responsible for receiving, conditioning, processing, analyzing, and storing the data received from the communication modules 119 from a plurality of buoys. It includes a plurality of statistical analysis methods, digital signal processing methods, and data visualization methods.

The server module comprises a web-enabled platform system capable of storing, analyzing, and visualizing all the parameters obtained from a plurally of buoys deployed. It includes numerical analysis, customized reports in table and graphical form, and chronological trending capabilities.

A.13 Renewable Energy and Power Circuit Module According to One Embodiment.

This module comprises the power systems responsible for supplying the power to the buoy 110. These include photovoltaic systems to collect sun energy, charge regulators and batteries 310 with an optimized vertical rotation wind microgenerator, and a "Neptune blower", based in wind generation due to the marine surface fluctuations in the inside of a pipe by the action of the swell. The system is based on the principle that the wind generated is projected over a vertical wind microgenerator. The power equipment dimensions is directly dependent of the consumption planned and these derived from the number of sensors, the sampling depths needed and the data transmission period.

According to one embodiment the buoy is equipped with a plurality of renewable energy capture capabilities, including a plurality of photovoltaic collectors 104, a wind microgenerator 234, and a wave microgenerator 306. These systems are designed to provide a stable and robust source of energy for the smart buoy even in the most difficult conditions due to the intrinsic diversification of sources. For instance, bad weather conditions may cause a significant reduction of photovoltaic energy but this situation is typically coupled with larger winds and waves, thus the other two sources are capable of compensating.

The power module includes a system capable of combining energy from a plurality of renewable energy sources 300 while maintaining the power quality required for the electronics systems comprising the smart buoy. This module includes a regulator 252 to produce a plurality of stable output DC voltages. FIG. 23 illustrates a block diagram including the different electronics modules comprising the buoy according to one embodiment.

A.10 Sensors Self-Cleaning Module According to One Embodiment.

According to one embodiment, the sensors self-cleaning module is comprised of a plurality of containers including cleaning liquids, fresh water, and additives. These containers are located in the surface, inside the buoy frame box 102 of the buoy. A pipe drives the cleaning liquid to the front of the sensors and an atomizer device that guarantees the liquid delivery over all the sensors with the necessary pressure to clean the sensitive zone of the sensor with a minimum liquid consumption.

Description of Operation: The sensors are self-cleaned by means of disposing the plurality of cleaning liquids, fresh water, and water with additives to the sensors at the appropriate pressure provided by the comp the compressor 114. The cleaning sessions are executed following a pre-programmed temporal schedule or on-demand. The control module 118 manages the default number of cleaning cycles as a function of time, number of readings conducted, available cleaning liquids, power available, and meteorological conditions.

A.11 Sensor Self-Calibration Module According to One Embodiment.

According to one embodiment, the sensors self-calibration module is comprised of a plurality of compartments and containers to store the a plurality of calibrating liquids. Each compartment includes a pipe with an associated electrovalve in order to fill the compartment and conduct the calibration. The buoy includes as many compartment and containers as calibrating liquids are required for a particular application involving a certain plurality of sensors requiring specific calibration liquids and routines.

Description of Operation: According to one embodiment, the self-calibration sessions follow the same steps as required during regular reading/analysis of water samples by the sensors but instead of sample water the sensors are immersed on calibration liquid 260 in this case.

The specific calibration liquid 260 needed for a particular sensor or set of sensors is supplied from the calibration compartment to the reading compartment 106 by means of an electrovalve. The sensors analyze the calibration liquid with known properties, the data is transmitted to the server, analyzed, and a calibration table and analysis is obtained. The self-calibration session can be executed following a pre-programmed temporal schedule or on-demand. The control module 118 manages the default number of calibration cycles as a function of time, number of readings conducted, available cleaning liquids, power available, and meteorological conditions.

A.12 Samples Storage Module According to One Embodiment.

According to one embodiment, the samples storage module comprises a revolving platform 116 including a plurality of sampling containers and a flat top with a hole where a pipe supplies the water sample to be stored by means of special pump 120. This sample comes from the reading compartment 106.

The function of the storage compartment 106 is controlled by the control module 118 or can be activated from distance using the communication system using the remote-controlled buoy capabilities. Its activation involves using the pump in order to capture the water from the reading compartment 106 and depositing it on the sampling container. Once the sampling container is full, the based rotates in order to fill additional containers. These samples are stored and the associated information is sent to the server including date, time, water depth, container identification number, as well as sensor 202 or 230 data.

Automatic scheduled sampling processes are programmed based on analytic gradient values from the sensors, by using scheduled times or on demand directly from the server.

A.13 Sensor Types According to One Embodiment.

According to one embodiment and without limitation, the buoy is designed to accommodate the following sensor types inside the isolated and environmentally protected sensor compartment, as well as incorporating the self-calibration liquids and self-cleaning fluids to perform their self-maintenance.

Sensor types for analysis in the buoy comprise temperature sensors, PH sensors, pressure (water depth) sensors, conductivity sensors, salinity sensors, fluorescence sensors, ORP sensors, dissolved oxygen sensors; hydrocarbons sensors, nitrates sensors, transmittance sensors, resistivity sensors, TDS sensors (total dissolved solids), specific gravity of seawater, sound velocity, wave sensors (accelerometers), photometer sensors, microscopic particle counter, turbulence sensors, and coriflias sensors.

Additionally, according to one embodiment the buoy supports also meteorological sensors 322 such as ambient temperature, humidity, barometric pressure, wind speed and direction, photometer, and video cameras.

According to one embodiment the smart buoy uses both the meteorological sensors as well as a plurality of built in accelerometers, inertial sensors, and wave sensors to determine if the environmental conditions are too rough and dangerous to take multi-depth water samples at the scheduled time safely. If the buoy determines the meteorological conditions are unsafe it will enter into a safety mode to protect itself and report the conditions the inland server. In these situations it is up to the human operator to review the conditions reported by the buoy sensors and determine whether to request on-demand samples, calibrations, or self-cleaning operations.

B. Operation

Due to its modularity the disclosed buoy can be implemented using a plurality of embodiments. For instance, the system of collecting/sampling multi-depth water by means of a hosepipe 108 comprising a plurality of independent pipes 220 with sampling inlets 126 at a plurality of water depths can be based on a mechanic, a hydrostatic, or pneumatic pumping system 232 designed to pump the sampled water to an isolated reading module 106.

According to one embodiment the sampling system and operation is based on hydrostatic pressure under the surface and emptying the circuit by compressed air. According to a second embodiment, the sampling system and operation is based on pumping under the surface and emptying the circuit by compressed air. This embodiment requires a plurality of pumps 232. According to a third embodiment, the sampling system and operation is based on peristaltic pumps under the surface.

While particular embodiments have been described, it is understood that, after learning the teachings contained in this disclosure, modifications and generalizations will be apparent to those skilled in the art without departing from the spirit of the disclosed embodiments. It is noted that the foregoing examples have been provided merely for the purpose of explanation and are in no way to be construed as limiting. While the system has been described with reference to various embodiments, it is understood that the words which have been used herein are words of description and illustration, rather than words of limitations. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. An apparatus for water sampling and analysis, said apparatus comprising:
   (a) a device for water sampling at one or more of depths comprising a hosepipe and one or more internal independent pipes with one or more sampling inlets at one or more water depths, and
   (b) a pumping system to pump a sample of water collected using said device for water sampling at one or more depths to an isolated module for analysis; and
   (c) a system for remote maintenance comprising a plurality of antifouling coatings and a self-cleaning system.

2. The apparatus of claim 1, wherein said pumping system is a mechanic pumping system.

3. The apparatus of claim 1, wherein said pumping system is a hydrostatic pumping system.

4. The apparatus of claim 1, wherein said pumping system is a pneumatic pumping system.

5. The apparatus of claim 1, wherein said isolated module comprises a plurality of analysis sensors protected from environmental agents.

6. The apparatus of claim 1, wherein said system for remote maintenance comprising a plurality of antifouling coatings and a self-cleaning system, further comprises a control module.

7. The apparatus of claim 6, wherein said system for remote maintenance further comprises a self-calibration system.

8. The apparatus of claim 7, wherein said system for remote maintenance comprises a plurality of self-cleaning containers including a plurality of cleaning liquids, fresh water, additives, calibration liquids, and a control module.

9. The apparatus of claim 8, wherein said control module in said system for remote maintenance performs self-cleaning and self-calibration based on:
   (a) a pre-programmed temporal schedule for maintenance;
   (b) an on-demand remote request; and
   (c) a function of the number of calibration cycles as a function of 1) time, 2) number of readings, and 3) available cleaning liquids, power, and meteorological conditions.

10. The apparatus of claim 9, further comprising a system for collecting, analyzing, storing, and transmitting monitoring data at pre-programmed time intervals or on-demand by means of two-way communications and remote control.

11. The apparatus of claim 10, further comprising a plurality of renewable energy sources.

12. The apparatus of claim 11, wherein said renewable energy sources comprise a photovoltaic module, a wind module, and a wave module.

13. A buoy for water sampling and analysis, said buoy comprising:
   (a) a device for water sampling at a plurality of depths comprising a hosepipe and a plurality of internal independent pipes with a plurality of sampling inlets at a plurality of water depths;
   (b) a pumping system to pump a sample of water collected using said device for water sampling at a plurality of depths to an isolated module for analysis;
   (c) a system for remote maintenance comprising a 1) plurality of antifouling coatings, 2) a self-cleaning system, and 3) a self-calibration system;
   (d) a system for collecting, analyzing, storing, and transmitting monitoring data at pre-programmed time intervals or on-demand by means of two-way communications and remote control; and
   (e) a plurality of renewable energy sources.

14. The buoy of claim 13, wherein said pumping system is chosen from the group consisting of mechanic pumping systems, hydrostatic pumping systems, and pneumatic pumping systems.

15. The buoy of claim 13, wherein said system for remote maintenance comprises a plurality of self-cleaning containers including a plurality of cleaning liquids, fresh water, additives, calibration liquids, and a control module.

16. The buoy of claim 13, wherein said control module in said system for remote maintenance performs self-cleaning and self-calibration based on:
   (a) a pre-programmed temporal schedule for maintenance;
   (b) an on-demand remote request; and
   (c) a function of the number of calibration cycles as a function of 1) time, 2) number of readings, and 3) available cleaning liquids, power, and meteorological conditions.

17. The buoy of claim 13, said renewable energy sources comprise a photovoltaic module, a wind module, and a wave module.

* * * * *